US012691079B2

(12) United States Patent
Benhabbour et al.

(10) Patent No.: US 12,691,079 B2
(45) Date of Patent: Jul. 28, 2026

(54) BIODISSOLVABLE FILM FOR LOCALIZED AND EFFICIENT TREATMENT OF VULVODYNIA

(71) Applicant: The University of North Carolina at Chapel Hill, Chapel Hill, NC (US)

(72) Inventors: Soumya Rahima Benhabbour, Chapel Hill, NC (US); Erin T. Carey, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 69 days.

(21) Appl. No.: 17/769,042

(22) PCT Filed: Oct. 15, 2020

(86) PCT No.: PCT/US2020/055816
§ 371 (c)(1),
(2) Date: Apr. 14, 2022

(87) PCT Pub. No.: WO2021/076778
PCT Pub. Date: Apr. 22, 2021

(65) Prior Publication Data
US 2024/0099984 A1 Mar. 28, 2024

Related U.S. Application Data

(60) Provisional application No. 62/915,452, filed on Oct. 15, 2019.

(51) Int. Cl.
| | |
|---|---|
| *A61K 9/70* | (2006.01) |
| *A61K 9/00* | (2006.01) |
| *A61K 31/167* | (2006.01) |
| *A61K 47/38* | (2006.01) |
| *A61K 47/42* | (2017.01) |
| *A61P 29/00* | (2006.01) |

(52) U.S. Cl.
CPC .......... *A61K 9/7007* (2013.01); *A61K 9/0034* (2013.01); *A61K 31/167* (2013.01); *A61K 47/38* (2013.01); *A61K 47/42* (2013.01); *A61P 29/00* (2018.01)

(58) Field of Classification Search
CPC ........................................................ A61P 29/00
See application file for complete search history.

(56) References Cited

U.S. PATENT DOCUMENTS

| | | | | |
|---|---|---|---|---|
| 5,800,832 | A * | 9/1998 | Tapolsky | A61K 47/38 |
| | | | | 424/448 |
| 6,375,963 | B1 | 4/2002 | Repka et al. | |
| 9,585,961 | B2 * | 3/2017 | Barnhart | A61K 47/38 |
| 2004/0151774 | A1 | 8/2004 | Pauletti et al. | |
| 2006/0018951 | A1 | 1/2006 | Maniar et al. | |

| | | | |
|---|---|---|---|
| 2016/0101061 | A1 | 4/2016 | Tapolsky et al. |
| 2017/0224749 | A1 * | 8/2017 | Palmeira De Oliveira ................. A61K 31/7056 |
| 2018/0036251 | A1 * | 2/2018 | Bogdahn .............. A61K 31/196 |

FOREIGN PATENT DOCUMENTS

| | | |
|---|---|---|
| CA | 2470102 A1 | 6/2003 |

OTHER PUBLICATIONS

De Andres et al. "Vulvodynia—An Evidence-Based Literature Review and Proposed Treatment Algorithm", Pain Pract. Feb. 2016;16(2):pp. 1-33. (Year: 2016).*
International Preliminary Report on Patentability corresponding to International Application No. PCT/US2020/055816 dated Apr. 28, 2022.
International Search Report and Written Opinion of the International Searching Authority corresponding to International Application No. PCT/US2020/055816 dated Jan. 6, 2021.
Research Grant, Nov. 6, 2017. "NIH Funding Opportunities and Notices in the NIH Guide for Grants and Contracts: Multidisciplinary Research in Vulvodynia (R01) PA-16-102." Feb. 17, 2016. Available from: https://grants.nih.gov/grants/guide/pa-files/pa-16-102.html.
Abo Enin et al., "Treatment of Radiation-Induced Oral Mucositis Using a Novel accepted Taste of Prolonged Release Mucoadhesive Bi-medicated Double-Layer Buccal Films." AAPS PharmSciTech, vol. 18(2), pp. 563-575 (2017).
Aerts et al., "Are Primary and Secondary Provoked Vestibulodynia Two Different Entities? A Comparison of Pain, Psychosocial and Sexual Characteristics." J. Sex. Med., vol. 12(6), pp. 1463-1473 (2015).
Akil et al., "Formulation and Characterization of Polymeric Films Containing Combinations of Antiretrovirals (ARVs) for HIV Prevention." Pharm. Res., vol. 32(2), pp. 258-468 (2015).
Button et al., "Roles of mucus adhesion and cohesion in cough clearance." PNAS, vol. 115(49), pp. 12501-12506 (2018).
Bunge et al., "A Phase 1 Trial to Assess the Safety, Acceptability, Pharmacokinetics, and Pharmacodynamics of a Novel Dapivirine Vaginal Film." JAIDS J. Acq. Imm. Def. Syndr., vol. 71(5), pp. 498-505 (2016).
Bornstein et al., "2015 ISSVD, ISSWSH, and IPPS Consensus Terminology and Classification of Persistent Vulvar Pain and Vulvodynia." J. Sex. Med., vol. 13(4), pp. 607-612 (2016).
Chowdary et al., "Dissolution, Bioavailability and Ulcerogenic Studies on Solid Dispersions of Indomethacin in Water Soluble Cellulose Polymers." Drug Dev. Ind. Pharm., vol. 20(5), pp. 799-813 (1994).
Ciszek et al., "MicroRNA expression profiles differentiate chronic pain condition subtypes." Transl. Res., vol. 166(6), pp. 706-720. e711 (2015).

(Continued)

*Primary Examiner* — Carlos A Azpuru
*Assistant Examiner* — Casey S Hagopian
(74) *Attorney, Agent, or Firm* — KDW FIRM PLLC

(57) ABSTRACT

Provided are biodissolvable films for localized treatment of a disorder of the female genital tract. The biodissolvable films are made of polymers forming a film suitable for application to a tissue of a female genital tract, where the film has a mucoadhesive property. Such films further include an active ingredient integrated and/or loaded into the biodissolvable film. Methods of treating inflammatory, atrophic and/or irritative disorders, including Vestibulodynia (VBD), are also provided.

18 Claims, 28 Drawing Sheets

(56) References Cited

OTHER PUBLICATIONS

Committee Opinion No. 673, "Persistent vulvar pain." American College of Obstetricians and Gynecologists. Obstet. Gynecol., vol. 128, pp. e78-e84 (2016).

Cook et al., "Polymeric gels intravaginal drug delivery." J. Control. Release, vol. 270, pp. 145-157 (2018).

Fan et al., "Preferred Physical Characteristics of Vaginal Film Microbicides for HIV Prevention in Pittsburgh Women." Arch. Sex Behav., vol. 46, pp. 1111-1119 (2017).

Gipson et al., "The Amount of MUC5B Mucin in Cervical Mucus Peaks at Midcycle 1." vol. 86(2), pp. 594-600 (2001).

Goldstein et al., "Vulvodynia: Assessment and Treatment." J. Sex Med., vol. 13(4), pp. 572-590 (2016).

Goodell et al., "Adhesive and Cohesive Peel Force Measurement of Human Airway Mucus." Bio-protocol, vol. 9(13), Article ID e3287 (14 pages) (2019).

Haefner et al., "The vulvodynia guideline." J. Low. Genit. Tract Dis., vol. 9(1), pp. 40-51 (2005).

Harlow et al., "A population-based assessment of chronic unexplained vulvar pain: have we underestimated the prevalence of vulvodynia?" J. Am. Med. Women's Assoc., vol. 58(2), pp. 82-88 (2003).

Johal et al., "Advanced topical drug delivery system for the management of vaginal candidiasis." Drug Deliv., vol. 23(2), pp. 550-563 (2016).

Karki et al., "Thin films as an emerging platform for drug delivery." Asian J. Pharm. Sci., vol. 11(5), pp. 559-574 (2016).

Landry et al., "The Treatment of Provoked Vestibulodynia." Clin. J. Pain, vol. 24(2), pp. 155-171 (2008).

Lev-Sagie et al., "Recent advances in understanding provoked vestibulodynia." vol. 5, Article No. 2581 (2016).

Machado et al., "Vaginal Films for Drug Delivery." vol. 102(7), pp. 2069-2081 (2013).

Mandal et al., "Guidelines for the management of vulvodynia." Br. J. Dermatol., vol. 162(6), pp. 1180-1185 (2010).

Notario-Perez et al., "Development of mucoadhesive vaginal films based on HPMC and zein as novel formulations to prevent sexual transmission of HIV." Intl. J. Pharm., vol. 570, Article No. 118643 (2019).

Padula et al., "In vitro evaluation of mucoadhesive films for gingival administration of lidocaine." AAPS PharmSciTech, vol. 14(4), pp. 1279-1283 (2013).

Preis et al., "Design and evaluation of bilayered buccal film preparations for local administration of lidocaine hydrochloride." Eur. J. Pharm. Biopharm., vol. 86(3), pp. 552-561 (2014).

Pukall et al., "Vulvodynia: Definition, Prevalence, Impact, and Pathophysiological Factors." J. Sex. Med., vol. 13(3), pp. 291-304 (2016).

Pukall, "Primary and Secondary Provoked Vestibulodynia: A Review of Overlapping and Distinct Factors." Sex. Med. Rev., vol. 4(1), pp. 36-44 (2016).

Roh et al., "The in vitro and in vivo effects of a fast-dissolving mucoadhesive bi-layered strip as topical anesthetics." Dent. Mater. J., vol. 35(4), pp. 601-605 (2016).

Shaikh et al., "Mucoadhesive drug delivery systems." J. Pharm. Bioallied Sci., vol. 3, pp. 89-100 (2011).

Sobel, "Patient education: Vaginal discharge in adult women (Beyond the Basics)." UpToDate.com (2016).

Sorensen et al., "Evaluation and Treatment of Female Sexual Pain: A Clinical Review." Muacevic, Adler, eds., Cureus, vol. 10(3), Article ID e2379 (12 pages) (2018).

Valenta, "The use of mucoadhesive polymers in vaginal delivery." Adv. Drug Deliv. Rev., vol. 57(11), pp. 1692-1712 (2005).

Zhang et al., "Dissolution mechanism of cellulose in N, N-dimethylacetamide/lithium chloride: revisiting through molecular interactions." J. Phys. Chem. B, vol. 118(31), pp. 9507-9514 (2014).

Zolnoun et al., "Overnight 5% lidocaine ointment for treatment of vulvar vestibulitis." Obstet. Gynecol., vol. 102(1), pp. 84-87 (2003).

Zolnoun et al., "Somatization and psychological distress among women with vulvar vestibulitis syndrome." Int. J. Gynaecol. Obstet., vol. 103(1), pp. 38-43 (2008).

Sobel, "Patient education: Vaginal discharge in adult women (Beyond the Basics)." UpToDate.com (2022).

Canadian Office Action in CA Application No. 3154465 dated Mar. 2, 2026, 10 pages.

* cited by examiner

Effect of Dissolution Media Volume

Effect of Polymer Content

Effect of Wet Casted Thickness

Effect of Drug Loading

1% HPMC

1.5% HPMC

3% HEC

5% HEC

7% HPC

9% HPC

3% HEC - Dissolution & Drug Release

3% HEC - Dissolution & Drug Release - 5 min

7% HPC - Dissolution & Drug Release

7% HPC - Dissolution & Drug Release - 30min

BIODISSOLVABLE FILM FOR LOCALIZED AND EFFICIENT TREATMENT OF VULVODYNIA

CROSS-REFERENCE TO RELATED APPLICATIONS

This application claims benefit of U.S. Provisional Patent Application Ser. No. 62/915,452, filed Oct. 15, 2019, herein incorporated by reference in its entirety.

This invention was made with government support under Grant Number TR002489 awarded by the National Institutes of Health. The government has certain rights in the invention.

TECHNICAL FIELD

The presently disclosed subject matter is directed to mucoadhesive thin films and/or mucoadhesive drug delivery platforms. More particularly, presently disclosed subject matter is directed to biodissolvable films for localized and efficient treatment of vulvodynia and related conditions.

BACKGROUND

Vestibulodynia (VBD) is the most common cause of sexual pain, affecting 10 to 28% of reproductive aged women (Sorensen et al., 2018; Pukall et al., 2016) in the United States yet remains ineffectively treated by standard trial-and-error approaches. The pain is chronic, lasting over 3 months, and compromises psychological functioning, interpersonal relations, and daily activity. As further evidence of its public health significance, VBD and related vulvar pain conditions cost the US economy over $70 billion annually. Two distinct VBD subtypes that may benefit from different types of treatment has been described: 1) VBD peripheral (VBD-p) subtype characterized by localized pain specific to the vulvar vestibule (Bornstein et al., 2016), and 2) VBD central (VBD-c) subtype characterized by pain at both vaginal and remote body regions. Sensitization of the peripheral vestibular nerves has been suggested as a possible pain mechanism vulvodynia. First-line treatment for both groups include the application of a lidocaine ointment, cream or gel to the vulvar vestibule once or twice daily prior to vulvovaginal manipulation (tampon use, intercourse, tight clothing) which can reduce symptoms and allow vaginal penetration. Lidocaine is short-acting and provides relief for 30-60 minutes.

One of the first-line treatments for VBD, topical lidocaine 5% ointment, cream or gel, is difficult to apply due to the content and lack of a directed delivery. Currently available topical 5% lidocaine has been highlighted as an effective treatment for VBD (Sorensen et al., 2018; Mandal et al., 2010) however the inability to apply the topical treatment to the vulvar vestibule and short duration of treatment (Johal et al.) makes this an important focus in delivery system development. Innovative vestibule medication delivery systems are needed to permit long-term, effective and directed therapy. Such needs are addressed by the instant disclosure.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided are biodissolvable films for localized treatment of a disorder of the female genital tract. The biodissolvable films can comprise a polymer forming a film suitable for application to a tissue of a female genital tract, wherein the film comprises a mucoadhesive property, and an active ingredient integrated and/or loaded into the biodissolvable film. In some embodiments, the polymer is a cellulose-based polymer selected from the group consisting of hydroxypropyl cellulose (HPC), hydroxypropyl methylcellulose (HPMC), hydroxyethyl cellulose (HEC), carboxymethyl cellulose (CMC) and combinations thereof. In some embodiments, the HEC further comprises a high molecular weight hydroxyethyl cellulose (HMW HEC) of about 250 kDa, or a low molecular weight hydroxyethyl cellulose (LMW HEC) of about 90 kDa. In some embodiments, the cellulose-based polymer forming the film comprises about 1% w/w HPMC, about 1.5% w/w HPMC, about 3% w/w HMW HEC, about 5% w/w HMW HEC, about 5% w/w LMW HEC, about 7% w/w LMW HEC, about 7% w/w HPC, or about 9% w/w HPC. In some embodiments, the film comprises a polymer selected from the group consisting of polyvinyl pyrrolidone (PVP), polyvinyl alcohol (PVA), polyethylene oxide (PEO), chitosan, alginate, carrageenan, gelatin and combinations thereof.

In some aspects, the biodissolvable films form a substantially u-shaped profile or substantially v-shaped profile, optionally wherein the biodissolvable film comprises a shape corresponding to a vulva of a subject. In some embodiments, the profile of the biodissolvable film is a of a size ranging from about 3 cm to about 5 cm long, and about 2 cm to about 4 cm wide.

In some embodiments, the disclosed biodissolvable films have a wet thickness of about 2, 3, 4 or 5 mm. In some embodiments, the film has a viscosity in the range of about 50 cP to about 3,000 cP. In some embodiments, the biodissolvable film is substantially biocompatible as defined by causing less than about 5%, optionally less than about 1%, cell death and/or cell damage when exposed to a cell or tissue. In some embodiments, the biodissolvable film has an elasticity defined by a Young's modulus of about 0.01 MPa to about 3.0 MPa, a yield strength of about 4.0 MPa to about 9.0 MPa, and/or a percent strain of about 25% to about 85%. In some embodiments, the biodissolvable film has a mucoadhesive property defined as an adhesive force of about 50 MN/cm$^2$ to about 2,500 MN/cm$^2$.

In some embodiments, the active ingredient is loaded at a rate of about 3% to about 12%, optionally about 5% to about 10%. In some embodiments, the active ingredient has a dissolution rate defined as at least 75% dissolution in about 5 minutes to about 10 hours, optionally about 30 minutes to about 6 hours. In some embodiments, the active ingredient has a dissolution rate of about 100% dissolution in about 5 minutes or less, optionally a rapid dissolution rate. In some embodiments, the cellulose-based film further comprises mucin.

In some embodiments, the active ingredient has a dissolution rate of about 100% dissolution in about 120 min or more, optionally a sustained release rate. In some embodiments, the active ingredient is selected from the group consisting of local anesthetics (lidocaine, ropivacaine, bupivacaine, liposomal bupivacaine), anti-inflammatory (corti-costeroids-clobetasol, halobetasol, mometasone furoate), interferons, nonsteroidal topical immunomodulators/topical calcineurin inhibitors (tacrolimus, macrolactams, pimecro-limus), nonsteroidal anti-inflammatory drugs (aspirin, ibu-profen, indomethacin, phenylbutazone, bromfenac, fenamate, sulindac, nabumetone, ketorolac, and naproxen), COX-2 or COX-1 inhibitors (naproxen, ketoprofen, ketoro-lac, indomethacin, diclofenac, teroxicam, celecoxib, meloxi-cam and flosulide), antimicrobials (metronidazole, clin-damycin, tetramycin, erythromycin, doxycycline, lumefloxacin, norfloxacin, ciprofloxacin, levofloxacin, nitrofurantoin, azithromycin, cefuroxime, sulfamethoxa-zole/trimethoprim and doxycycline), antifungals (micona-zole, terconazole, isoconazole, fenticonazole, tioconazole, fluconazole, nystatin, ketoconazole, clotrimazole, butocona-zole, econazole, metronidazole and itraconazole), antiviral compounds (herpes, human papilloma virus, HIV), phyto-cannabinoids, anticonvulsants, antidepressants (tricyclic antidepressants such as amitriptyline, desipramine and nor-triptyline; SSRIs, SNRIs), NMDA receptor antagonists (dextromethorphan, ketamine, phencyclidine, methoxet-amine, and nitrous oxide), neuropeptide releasing agents (i.e. capsacian), muscle relaxants (methocarbamol, cyclobenzaprine, carisoprodol, metaxalone, tizanidine, baclofen, oxazepam), calcium channel blockers (diltiazem, israpidine, nimodipine, felodipine, verapamil, nifedipine, nicardipine, and bepridil), vasodilators (nitroglycerin, isosorbide dinitrate, and isosorbide mononitrate), sodium channel blockers, potassium channel blockers (dofetilide, almokalant, sematilide ambasilide, azimilide, tedisamil, sotalol, piroxicam and ibutilide), beta blockers, alpha block-ers, benzodiazepines (diazepam, clonazepam, alprazolam, estazolam, lorazepam), hormone therapy (estrogen deriva-tives, testosterone, DHEA, progesterone), levothyroxine, praxomine, antihistamines (i.e. diphenhydramine, fexofena-dine, hydroxyzine, chlorpheniramine, desloratadine, lorata-dine, doxylamine, carbinoxamine), cromolyn sulfate, meth-ylene blue, botulinum toxin, therapeutics for pre/post-surgical application, therapeutics for wound care following vaginal delivery, edible oils (olive oil, walnut oil, coconut oil, avocado oil, sunflower oil), probiotics, cannabinoids/cannabis oil, evening primose, rose oil, fennel, aloe, chamo-mile extract, comfrey, arnica, cucumber, hemp, boric acid, and combinations thereof.

In some embodiments, the active ingredient comprises Lidocaine hydrochloride (LHC). In some embodiments, the biodissolvable film is configured to release LHC after absorption and provide relief to a subject for about 0.5 to about 4 hours.

In some embodiments, the biodissolvable film is config-ured to treat inflammatory, atrophic and/or irritative disor-ders of the female genital tract. In some embodiments, the biodissolvable film is configured to treat provoked vestibu-lodynia, vulvodynia, vulvar vestibulitis, dyspareunia, yeast candidiasis, bacterial vaginosis/bacterial vaginitis, hypoe-strogenic state/genital atrophy, lichen sclerosus, lichen pla-nus, lichen simplex chronicus, desquamative inflammatory vaginitis, cervicitis, cervical ectropion, dysmenorrhea, endo-metriosis, pelvic inflammatory disease, uterine leiomyoma, sexually transmitted infection, bacterial infections, yeast infections, hormone deficiencies, postsurgical scarring, vaginal discharge, pH imbalance, vaginal lubrication, vagi-nal moisturization, vulvar intraepithelial neoplasia vaginal intraepithelial neoplasia, endometrial intraepithelial neopla-sia, cervical intraepithelial neoplasia, prophylactic protection from the above conditions. In some embodiments, the biodissolvable film is configured to treat Vestibulodynia (VBD).

Provided herein are also kits comprising a biodissolvable film as disclosed herein, an applicator for applying the biodissolvable film to a subject, and optionally instructions for using the biodissolvable film.

In some embodiments, provided are methods of treating an inflammatory, atrophic and/or irritative disorders of the female genital tract, the method comprising providing a subject in need of treatment, and applying a biodissolvable film as disclosed herein to the subject. In some embodi-ments, the biodissolvable film is applied to the vulvar vestibule of the subject, optionally to the uterus, uterine cavity, vagina, vulva, perianal, perineal, rectal, cervical regions of the subject. In some embodiments, the inflam-matory, atrophic and/or irritative disorder comprises Ves-tibulodynia (VBD). In some embodiments, the subject is a female human.

These and other objects are achieved in whole or in part by the presently disclosed subject matter. Further, objects of the presently disclosed subject matter having been stated above, other objects and advantages of the presently dis-closed subject matter will become apparent to those skilled in the art after a study of the following description, Draw-ings and Examples.

BRIEF DESCRIPTION OF THE DRAWINGS

The presently disclosed subject matter can be better understood by referring to the following figures. The com-ponents in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organi-zation and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIG. 2A shows evaluation of cell damage with optimized film formulations using an LDH cytotoxicity assay. FIG. 2B shows cell viability of optimized film for-mulations using a CellTiter-Glo® luminescent cell viability assay (ATP assay). Cells in FIGS. 2A and 2B were incubated with individual films (4 mm diameter) for 24 h at 37° C. All experiments were done in triplicate. Statistical significance was determined using a two-tailed t-test compared to the negative control or 100% cell viability. Statistical significance is shown as: P≤0.05 *, P≤0.01 , P≤0.001 * P≤50.0001 ****.

FIG. 3A shows representative placebo samples were chosen for each film type. FIG. 3B shows percent strain at fracture for each film type. FIG. 3C shows yield strength for each film type. FIG. 3D shows Young's Modulus for each film type.

In FIG. 5A mucoadhesive properties of various placebo films (1 cm2 square) compared to control (1 cm2 square kimwipe) measured as the force (mN/cm2) exerted to remove the film sample from the mucus surface. All measurements were done in triplicate. Statistical analyses were done using an unpaired two-tailed t-test, and statistical significance is shown as: P≤0.05 *, P≤0.01 , P≤0.001 *, P≤0.0001 ****. FIG. 5B shows results of a peel test of mucus-film adhesive strength. Mucoadhesive properties of 5% HEC placebo film (1 cm$^2$ square) compared to LHC loaded 5% HEC (1 cm$^2$ square with 6% LHC) measured as the force (mN/cm$^2$) exerted to remove the film sample from the mucus surface. All measurements were done in triplicate.

FIG. 6A shows the effect of media volume on dissolution rate of 5% HEC placebo films. Films were incubated in 2 mL, 4 mL, or 8 mL of SVF+2% solutol at RT. FIG. 6B shows the effect of polymer content. Percent dissolution of 1% HPMC and 1.5% HPMC in 4 mL SVF+2% solutol at RT. FIG. 6C shows the effect of media pH on percent dissolution of 1.5% HPMC films. Films were incubated in 4 mL SVF+2% solutol (pH=4.2) or 4 mL of PBS+2% solutol (pH=7.4) at room temperature (RT). All studies were done in triplicate. FIG. 6D shows the effect of drug loading. Percent dissolution of 9% HPC films loaded with 6% lidocaine HCl and placebo films in 4 mL SVF+2% solutol at RT. FIG. 6E shows percent dissolution of HEC, HPC and HPMC films in 4 mL SVF+2% solutol at RT. FIG. 6F shows the effect of casting thickness on dissolution of 3% HEC. Films casted at 2 mm and 4 mm wet thickness were incubated in 4 mL SVF+2% solutol at RT. FIG. 6G shows the effect of mucin on dissolution of 7% HPC films. Films were incubated at RT in 4 mL SVF+2% solutol with 0.01% w/w mucin or without mucin.

FIG. 7A shows the effect of polymer type on drug release kinetics. Films were cast at 2 mm wet thickness with 6% LHC in the solution formulation. Within the first 5 minutes, a burst release is shown. FIG. 7B shows the effect of wet casting thickness on LHC release was determined using 9% HPC 6% LHC films casted at different wet thicknesses ranging from 2-5 mm. FIG. 7C shows the effect of drug loading on release kinetics was investigated using 9% HPC films with varying drug loading at 3%, 6%, and 12% LHC in the solution formulation. FIG. 7D shows drug loading and wet casting thickness were varied to demonstrate tunability using the 9% HPC films. All studies were done in triplicates.

DETAILED DESCRIPTION

Figure 1A:
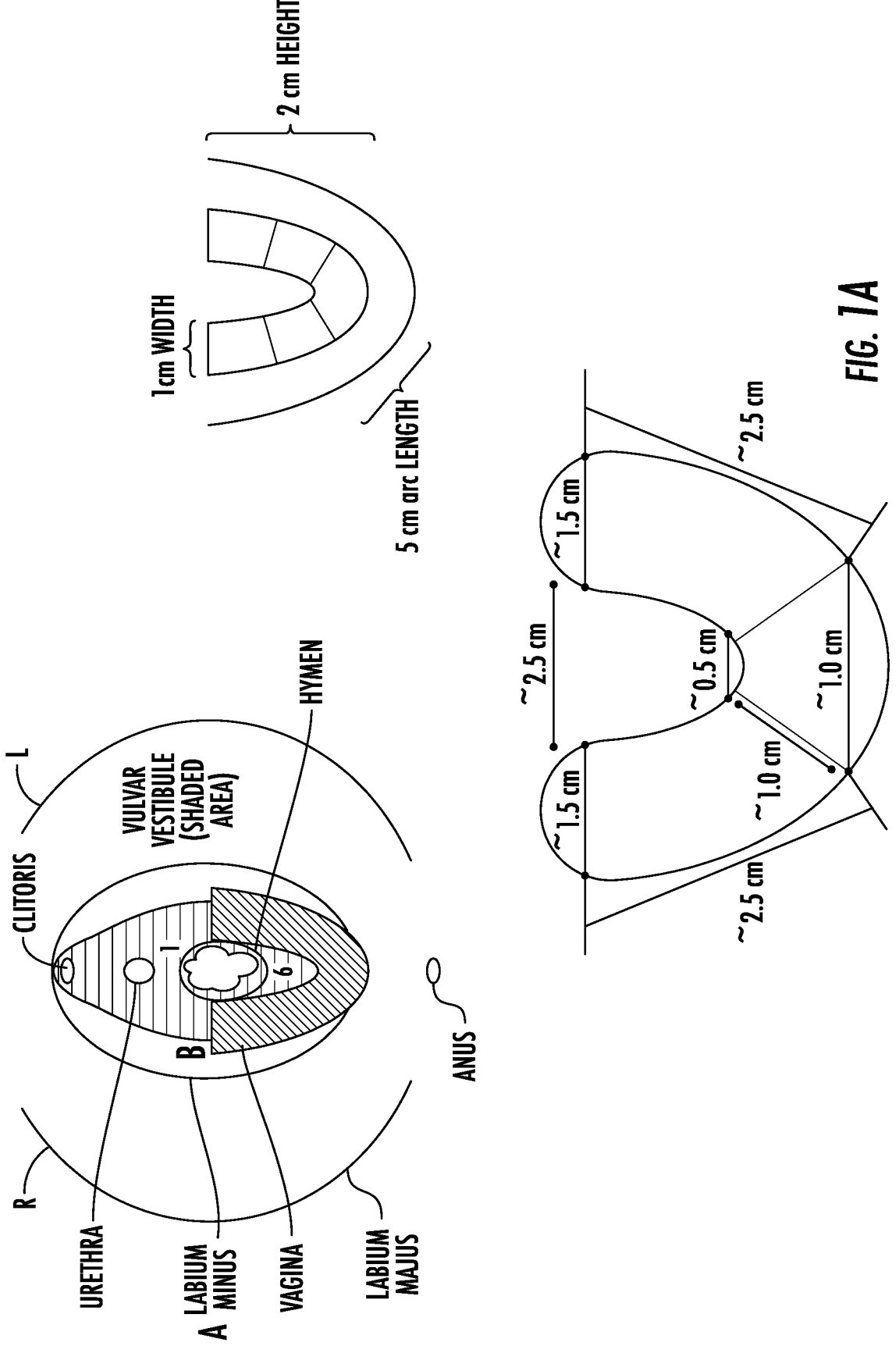
FIG. 1A is a schematic showing the area of inflammation and a film design to fit a range of vulvar sizes.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments 0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

II. Biodissolvable Films and Methods of Use

Provided herein is a novel mucoadhesive biodissolvable lidocaine film for localized and efficient treatment of VBD. There have been no drug delivery developments in the symptomatic treatment of vestibular pain. In fact, one of the most extreme treatments of VBD is surgical removal of the vulvar vestibule, including the surrounding perineal skin, the mucosa of the posterior vulvar vestibule and the posterior hymenal ring. The vagina must then be undermined and advanced to close the defect.

Reported success from this intervention is higher than other treatment options available, 60-90% success, however complications and risk of surgical intervention limit its standing as first or second line treatment. Surgical management of VBD is an option for management once less invasive treatment options have been employed. Disclosed herein is a novel mucoadhesive biodissolvable film, designed to be flexible enough to apply and adhere to the vulvar vestibule and allow for slow drug release of local anesthetic to the affected tissue for several hours. This drug delivery platform has never been used for treatment on the vulva, unique considerations of which required challenges to be overcome.

The present disclosure provides for the first time a mucoadhesive biodissolvable film technology to the vulvar vestibule. Based on patient anatomical measurements of the vulvar area, the present disclosure provides a film design (shape, size) to fit the area of inflammation and optimize contact with the vulva for improved therapeutic outcomes (FIG. 1A).

The present disclosure provides film casting that allows for the development of the disclosed drug-releasing biocompatible film. Film properties (e.g. polymer type, film thickness, drug loading) have also been optimized and designed to provide a range of release kinetics (e.g., <5 min→3 hr). Additionally, in vivo safety and pharmacokinetics (PK) of lidocaine films in BLAB/c mice with mouse-size films (4 mm OD) were assessed.

Thus, in some aspects, the disclosed biodissolvable films for localized treatment of a disorder of the female genital tract can comprise a polymer forming a film suitable for application to a tissue of a female genital tract, wherein the film comprises a mucoadhesive property, and an active ingredient integrated and/or loaded into the biodissolvable film. The polymer can be a cellulose-based polymer selected from the group consisting of hydroxypropyl cellulose (HPC), hydroxypropyl methylcellulose (HPMC), hydroxyethyl cellulose (HEC), carboxymethyl cellulose (CMC) and combinations thereof. The HEC can further comprise a high molecular weight hydroxyethyl cellulose (HMW HEC) of about 250 kDa, or a low molecular weight hydroxyethyl cellulose (LMW HEC) of about 90 kDa. The cellulose-based polymer forming the film can in some embodiments comprise about 1% w/w HPMC, about 1.5% w/w HPMC, about 3% w/w HMW HEC, about 5% w/w HMW HEC, about 5% w/w LMW HEC, about 7% w/w LMW HEC, about 7% w/w HPC, or about 9% w/w HPC. Additionally, in some embodiments, the film can comprise a polymer selected from the group consisting of polyvinyl pyrrolidone (PVP), polyvinyl alcohol (PVA), polyethylene oxide (PEO), chitosan, alginate, carrageenan, gelatin or a combination thereof.

Moreover, the disclosed sustained release mucoadhesive drug delivery system of the vulva can in some embodiments be impregnated with other medications to treat other vulvar skin and vaginal disorders. While the vulvar vestibule is a unique intersection of an embryologically distinct band of tissue between the internal female reproductive tract and external vulva, drug delivery to the vulva and vagina with the presently disclosed devices and components can be augmented and employed for inflammatory, atrophic and irritative disorders of the female genital tract, e.g. genital pain disorders and VBD.

The flexibility of the presently disclosed devices and systems provides for a biodissolvable film with a range of shapes/dimensions and having a range of physical/chemical properties to fit a wide range of health indications, e.g. women's health indications, and unmet needs that require external or internal vaginal delivery for prevention or treatment of infections or diseases.

By way of example and not limitation, conditions and diseases to be treated based on the instant disclosure include provoked vestibulodynia, vulvodynia, vulvar vestibulitis, dyspareunia, yeast candidiasis, bacterial vaginosis/bacterial vaginitis, hypoestrogenic state/genital atrophy, lichen sclerosus, lichen planus, lichen simplex chronicus, desquamative inflammatory vaginitis, cervicitis, cervical ectropion, dysmenorrhea, endometriosis, pelvic inflammatory disease, uterine leiomyoma, sexually transmitted infection, bacterial infections, yeast infections, hormone deficiencies, postsurgical scarring, vaginal discharge, pH imbalance, vaginal lubrication, vaginal moisturization, vulvar intraepithelial neoplasia, vaginal intraepithelial neoplasia, endometrial intraepithelial neoplasia, cervical intraepithelial neoplasia, prophylactic protection from the above conditions.

By way of example and not limitation, active ingredients, medications, compositions and therapeutics suitable for release from and/or administration by the disclosed devices, e.g. dissolvable film, include local anesthetics (lidocaine, ropivacaine, bupivacaine, liposomal bupivacaine), anti-inflammatory (corticosteroids-clobetasol, halobetasol, mometasone furoate), interferons, nonsteroidal topical immunomodulators/topical calcineurin inhibitors (tacrolimus, macrolactams, pimecrolimus), nonsteroidal anti-inflammatory drugs (aspirin, ibuprofen, indomethacin, phenylbutazone, bromfenac, fenamate, sulindac, nabumetone, ketorolac, and naproxen), COX-2 or COX-1 inhibitors (naproxen, ketoprofen, ketorolac, indomethacin, diclofenac, teroxicam, celecoxib, meloxicam and flosulide), antimicrobials (metronidazole, clindamycin, tetramycin, erythromycin, doxycycline, lumefloxacin, norfloxacin, ciprofloxacin, levofloxacin, nitrofurantoin, azithromycin, cefuroxime, sulfamethoxazole/trimethoprim and doxycycline), antifungals (miconazole, terconazole, isoconazole, fenticonazole, tioconazole, fluconazole, nystatin, ketoconazole, clotrimazole, butoconazole, econazole, metronidazole and itraconazole), antiviral compounds (herpes, human papilloma virus, HIV), phytocannabinoids, anticonvulsants, antidepressants (tricyclic antidepressants such as amitriptyline, desipramine and nortriptyline; SSRIs, SNRIs), NMDA receptor antagonists (dextromethorphan, ketamine, phencyclidine, methoxetamine, and nitrous oxide), neuropeptide releasing agents (i.e. capsacian), muscle relaxants (methocarbamol, cyclobenzaprine, carisoprodol, metaxalone, tizanidine, baclofen, oxazepam), calcium channel blockers (diltiazem, israpidine, nimodipine, felodipine, verapamil, nifedipine, nicardipine, and bepridil), vasodilators (nitroglycerin, isosorbide dinitrate, and isosorbide mononitrate), sodium channel blockers, potassium channel blockers (dofetilide, almokalant, sematilide ambasilide, azimilide, tedisamil, sotalol, piroxicam and ibutilide), beta blockers, alpha blockers, benzodiazepines (diazepam, clonazepam, alprazolam, estazolam, lorazepam), hormone therapy (estrogen derivatives, testosterone, DHEA, progesterone), levothyroxine, praxomine, antihistamines (i.e. diphenhydramine, fexofenadine, hydroxyzine, chlorpheniramine, desloratadine, loratadine, doxylamine, carbinoxamine), cromolyn sulfate, methylene blue, botulinum toxin, therapeutics for pre/postsurgical application, therapeutics for wound care following vaginal delivery, edible oils (olive oil, walnut oil, coconut oil, avocado oil, sunflower seed oil), boric acid, probiotics, cannabinoids/cannabis oil, evening primose, rose oil, fennel, aloe, chamomile extract, comfrey, arnica, cucumber, hemp.

An aspect of the presently disclosed subject matter is the unique anatomical location to which the medical devices are applied. The vulvar vestibule (between labia majora and labia minora) is lined by stratified squamous epithelium, non-keratinized to thinly keratinized tissue. This is a highly specific area of the genital tract. The cutaneous thickness and degree of keratinization vary widely on the external genitalia, a factor to delineate when describing and developing film application. The mons pubis and labia majora are highly keratinized, and this decreases over the clitoris and outer surface of the labia minora and even less keratinized on the inner portion of the labia minora. This highly variant keratinization in the lower genital tract is unique—the only area of the female anatomy where there is tissue from all three embryologic layers (ectoderm, endoderm and mesoderm). The mons pubis, labia, clitoris and perineum are derived from the ectoderm. The mucosa of the vulvar vestibule is the only portion of the female genital tract of endodermal origin. Histologically, the superficial stratum is non-keratinized with loosely packed polyhedral cells of varying sizes from the basal layer up. There is no clear area of demarcation as observed in the keratinized tissue of the vulva (FIG. 1A). Innervation of the vulvar area does not strictly correlate with embryonic development. It is highly nerve dense as well as having significant blood flow. Additionally, the vulvar epithelium is immunocompetent, with Langerhans cells being the most common immune cell. Allergic responses in vulvar skin are known contributors to chronic vulvar discomfort.

Notably, in some embodiments the disclosed devices and films can also extend to application on the uterus, uterine cavity, vagina, vulva, perianal, perineal, rectal, cervical regions. The devices, systems and/or films provided herein can be considered and/or referred to as cellulose-based mucoadhesive thin films and/or mucoadhesive drug delivery platforms.

Similar to the vagina, but unlike the vulva, the vestibular tissue also changes with the menstrual cycle. This can affect timing of the film application. The thickness, parakeratosis and glycogen content rise at midcycle. Thus, in some embodiments the film or the application process can be altered or adjusted across the menstrual cycle may be required to achieve similar results. The vaginal pH rises during menstruation as well.

In the setting of infection, the pH of the vaginal fluid/vagina and vestibule change in response to the level of lactic acid-producing microbes. As such, the dissolvable films disclosed herein can comprise various compounds to accommodate a range of pH from 4-8 of the vaginal fluid to allow for film dissolvability on the vestibule. In some aspects, a pH testing strip can be used prior to application to instruct the application product, and can be included in a kit along with one or more films/devices as disclosed herein.

The vulva, vagina and vestibule are sensitive to hormone cycling and applications will be developed to apply in pre and postmenopausal women. The estrogen content in the vulvar vestibule will affect the application process. Post-menopausal vulvovaginal atrophy/genitourinary syndrome of menopause is also an area for application. The thinned tissue is more easily irritated and may be more susceptible to infection. Unique to this group, the vaginal pH rises, increasing risk of vaginal and urinary tract infections. Certain vulvar dermatoses, such as lichen sclerosus, lichen planus, are most prevalent in peri- and post-menopausal women.

The disclosed films and/or devices can be applied or administered prior to sexual intercourse for pain prevention or simply as a barrier to semen. Semen itself can be a trigger of vestibular pain as an irritant. Such can also include a scheduled application for the prevention or treatment of the conditions disclosed herein.

Likewise, in some embodiments the disclosed films and medical devices can be used as a barrier during menstruation as blood can irritate the vestibule in some women.

In some aspects, the disclosed films and devices can be dissolvable and/or non-dissolvable (applied for direct medication release and then removed once medication absorbed), or substantially dissolvable and/or substantially non-dissolvable. The design of the film can be unique to and/or varies amongst women. Application and design for a product application of this u-shaped area between the labia minora and the vagina has not previously been described.

The vulvar vestibule rests between the labia minora and the vagina, and varies in size, but in general is u-shaped and approximately 4-7 cm in length and about 0.5-2 cm in width, narrowest at the six o'clock position (FIG. 1A). Women who experience pain often describe most symptoms between the 3 and 9 o'clock region (though the vestibule extends up past the urethra bilaterally). At least one aspect of the disclosed films and devices is the configuration suitable for application to this area, which can in some aspects improve functionality and efficacy for target therapies at this location.

Thus, for application in the endometrial cavity, the disclosed medical devices and films, as illustrated in FIG. 1A, can be about 3 to about 5 cm long, e.g. about 3, 3.5, 4, 4.5 or 5 cm, and about 2 to about 4 cm wide, e.g. about 2, 2.5, 3, 3.5 or 4 cm, in a heart shaped, v-shaped, u-shaped or similar configuration to fill the cavity. As shown in FIG. 1A, in some embodiments the devices can have a general u-shape with curved or rounded edges for comfort and fit, with a base portion (or lower/ventral portion) being about 1 cm wide with wings extending from each side at about 2.5 cm in length (about 1.5 cm wide). Additionally, in some aspects, the film/device can vary in size according to the vestibular size. As described, the vestibule is most narrow at the 6 o'clock or ventral position and widens at the tops, 0.5-2 cm posterior fourchette and 2-4 cm wings laterally to create the u-shape/v-shape of the female anatomy.

In some aspects, an applicator can be required to deploy the film into the cavity.

In some embodiments, for application on the cervix the film or device can be about 3 cm×3 cm, e.g. about 2.5, 3 or 3.5 cm, and round shaped, circular or oval-shaped.

For application in the vagina the film or device can be square or rectangle shaped at about 3 cm to about 4 cm×3 cm to about 4 cm.

The bioadhesive film can in some aspects have the ability to provide controlled release delivery of a drug or medication to skin, vestibule, mucosa, endometrium.

In some aspects the films and devices herein can be configured to adhere to mucosal surfaces and skin surfaces when wet according to the pH of the environment. The film can include a backing layer to protect it from dissolution prior to use. In some aspects, the patient can load the film into an applicator and remove the backing (similar to a dental whitening strip) and then separate the labia with one hand and gently press the applicator on the vestibule. This will deploy the film/device. An alternative is to have the patient directly apply the film to the vestibule without use of the applicator or have a provider or partner assist in application.

The dissolvable film product can in some aspects require additional solution to assist is dissolution. By way of example and not limitation, a saline product can be provided with the drug loaded film, i.e. in a kit. Once the film has dissolved the patient can assume her activities.

In some aspects, a non-dissolvable film/device can have a release tab, e.g. at the 6'oclock or lower position, to allow for easy removal once the drug has been released into the tissue.

In some aspects, the films and devices herein can have a drug-free backing layer to allow unidirectional drug diffusion into the target tissue.

In some aspects, each film can be a single use product, packed and sealed in a sterile individual container.

III. Subjects

The subject medical devices, e.g. biodissolvable films, are desirably suitable for human subjects, particularly female subjects, although it is to be understood that the principles of the disclosed subject matter indicate that the compositions and methods are effective with respect to invertebrate and to all vertebrate species, including mammals, which are intended to be included in the term "subject". Moreover, a mammal is understood to include any mammalian species in which screening is desirable, particularly agricultural and domestic mammalian species.

The disclosed devices and methods are particularly useful in the treatment of warm-blooded vertebrates. Thus, the presently disclosed subject matter concerns mammals and birds.

More particularly, provided herein are devices and treatments of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

In some embodiments, the subject to be used in accordance with the presently disclosed subject matter is a subject in need of treatment and/or diagnosis. In some embodiments, a subject can have or be believed to have/suffer from Vestibulodynia or related condition.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods for Examples 1-10

Materials

Hydroxypropyl cellulose (HPC, 100 kDa) and hydroxypropyl methylcellulose (HPMC, 110 kDa) were purchased from Alfa Aesar. High molecular weight hydroxyethyl cellulose (HMW HEC, 250 kDa) and low molecular weight hydroxyethyl cellulose (LMW HEC, 90 kDa) were purchased from Sigma-Aldrich. Plexiglass casting molds and metal cutters were custom made by the UNC Chapel Hill Machine Shop. Lidocaine Hydrochloride was purchased from Sigma-Aldrich. Sodium acetate was purchased from Fisher Scientific. Phosphate buffered saline (PBS) was purchased from Sigma-Aldrich. Kolliphor HS 15 (Solutol) was purchased from Sigma-Aldrich. Synthetic bovine mucin was purchased from Sigma-Aldrich. 0.1% trifluoroacetic acid (TFA) in water and 0.1% TFA in Acetonitrile were purchased from Fisher Chemical. Human leiomyosarcoma SK-LMS-1 cell line was purchased from American Type Culture Collection (ATCC HTB-88™ Manassas, VA). Fetal bovine serum (FBS) was purchased from EMD Millipore Corp. (Billerica, MA).

Film Formulation Optimization and Characterization

Hydroxypropyl cellulose (HPC, MW 100 kDa), hydroxypropyl methylcellulose (HPMC, MW 110 kDa), high molecular weight hydroxyethyl cellulose (HMW HEC, MW 250 kDa), and low molecular weight hydroxyethyl cellulose (LMW HEC, MW 90 kDa) were selected based on their known biocompatible and mucoadhesive properties to develop a lidocaine loaded mucoadhesive film for treatment of vestibulodynia (VBD). Each polymer was dissolved in deionized water (DI $H_2O$) at various weight percentages. The range of workable polymer weight percent in DI $H_2O$ was determined by measuring the viscosity of the polymer solution using a Brookfield Model DV-III+programmable. Polymer solutions with viscosity in the range of 50-3000 cP were used for film casting. Based on this viscosity range, eight formulations were initially investigated as potential candidates for film casting; 1% w/w HPMC, 1.5% w/w HPMC, 3% w/w HMW HEC, 5% w/w HMW HEC, 5% w/w LMW HEC, 7% w/w LMW HEC, 7% w/w HPC, and 9% w/w HPC. The density of each formulation was measured by weighing 1 mL of each polymer formulation in a 1 mL volumetric flask.

Figure 1B:
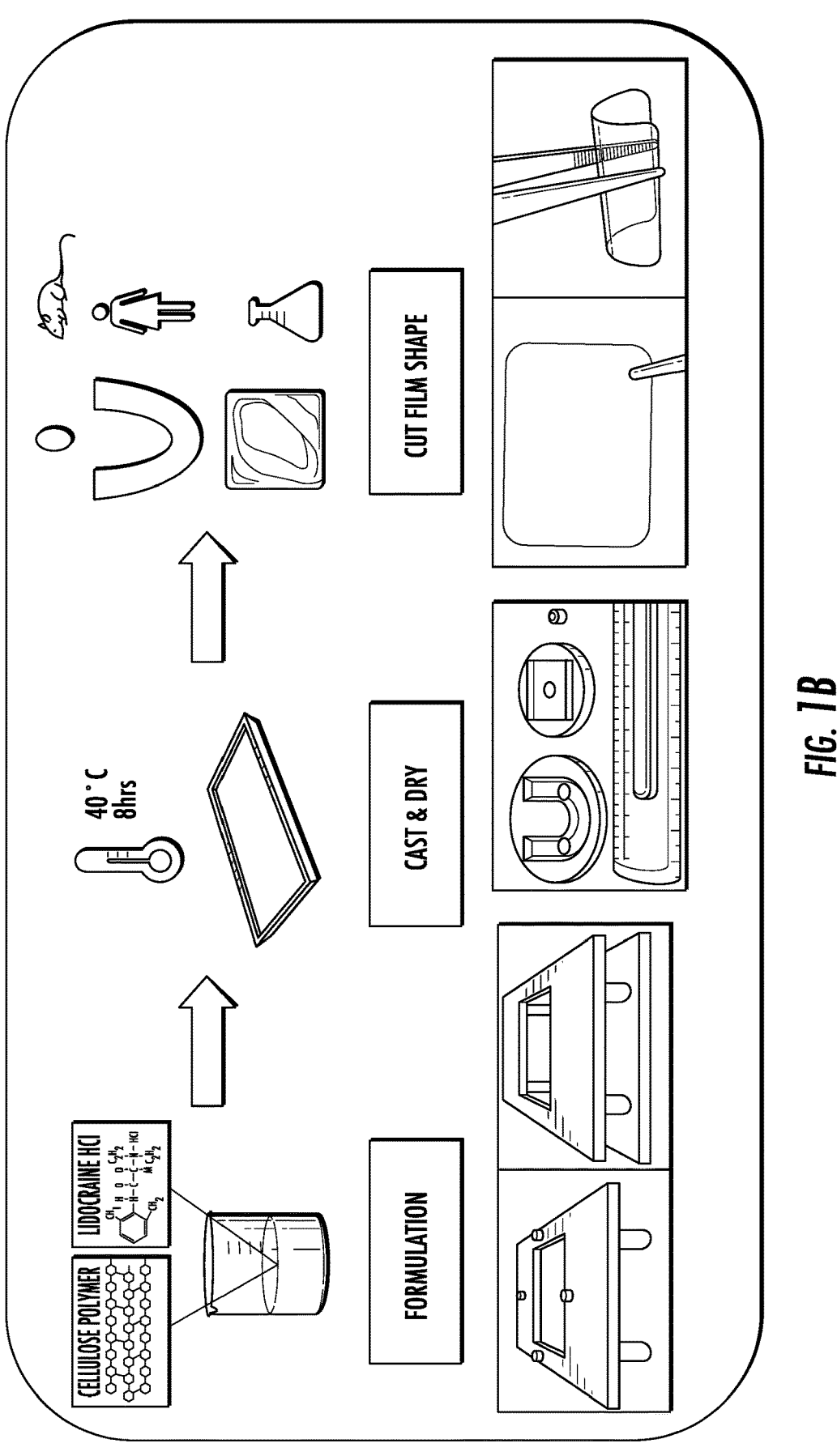
FIG. 1B shows thin films were fabricated using a solvent-casting method. Formulation solutions were prepared by solubiliz-ing polymer and drug in deionized water. The formulation solutions were poured into plexiglass molds and set to dry at 40° C. for 8 hrs, and then cut into desired shapes for experimental use.

Films were fabricated using an optimized solvent-casting method (FIG. 1B). In the first method, 20 g of polymer solution was poured onto a smooth plexiglass plate and set to a wet thickness of 2 mm using a BYK-Gardner Film Casting Knife. To minimize variability in film thickness and improve reproducibility in casted films, the casting method was modified to use custom-made plexiglass film casting molds. Film molds were built to have depths of 2, 3, 4, and 5 mm and consisted of two conjoining pieces, held together by screws, for efficient removal of dried thin films. For film casting, molds were filled completely with a polymer solution, and excess solution was removed by drawing a BYK-Gardner Film Casting Knife set to 0 mm over the top of the mold. All casted films were dried in an oven at 40° C. for 8 h. To evaluate and quantify the relationship between the wet polymer solution and the dried thin film, two methods were used: 1) a weight-based ratio and 2) a thickness-based ratio. Understanding these relationships between wet polymer solution and the resulting dried film allowed the final film properties to be tuned based on the initial casting parameters.

To determine the weight-based ratio between the wet casted polymer solutions and their respective dried thin films, each premade polymer solution (3% HMW HEC, 5% HMW HEC, 7% HPC, 9% HPC, 1% HPMC, and 1.5% HPMC) was weighed into a plastic petri dish at a predetermined weight of 1, 2, 3, 4, and 5 g in triplicate. These values were chosen to provide a range of dry films to test in subsequent studies. Initial sample weights of the polymer in the petri dish were recorded, and allowed to dry at 40° C. for 8 h. The resulting thin films were subsequently weighed to record their dry weight. The initial weight (wet polymer) was then compared to the final dry weight (thin film). These weights were used to calculate percent-mass loss from the initial wet polymer solution to the final dry film for each film formulation.

The relationship between the thickness of the wet casted polymer solution and corresponding dried thin films was determined by casting each formulation (3% HMW HEC, 5% HMW HEC, 7% HPC, 9% HPC, 1% HPMC, and 1.5% HPMC) at a wet thickness of 2, 3, 4, and 5 mm using custom made film casting molds and subsequent drying at 40° C. for 8 h. Dried films were removed from the plexiglass plates or molds and cut into samples for manipulation using a metal stamp and desktop press. The metal stamp was custom-made with dimensions of 2.24×2.24 $cm^2$ in order to create film samples with a surface area similar to the average surface area of the human vulva. Three 2.24×2.24 $cm^2$ samples were cut from each film and measured for dried thickness in triplicate using a Mitutoyo digital micrometer. The relationship between the dried film thickness and original wet casted thickness was determined for each polymer formulation to assess variability across the casting molds and polymer types.

Mucoadhesion Studies

Figure 10:
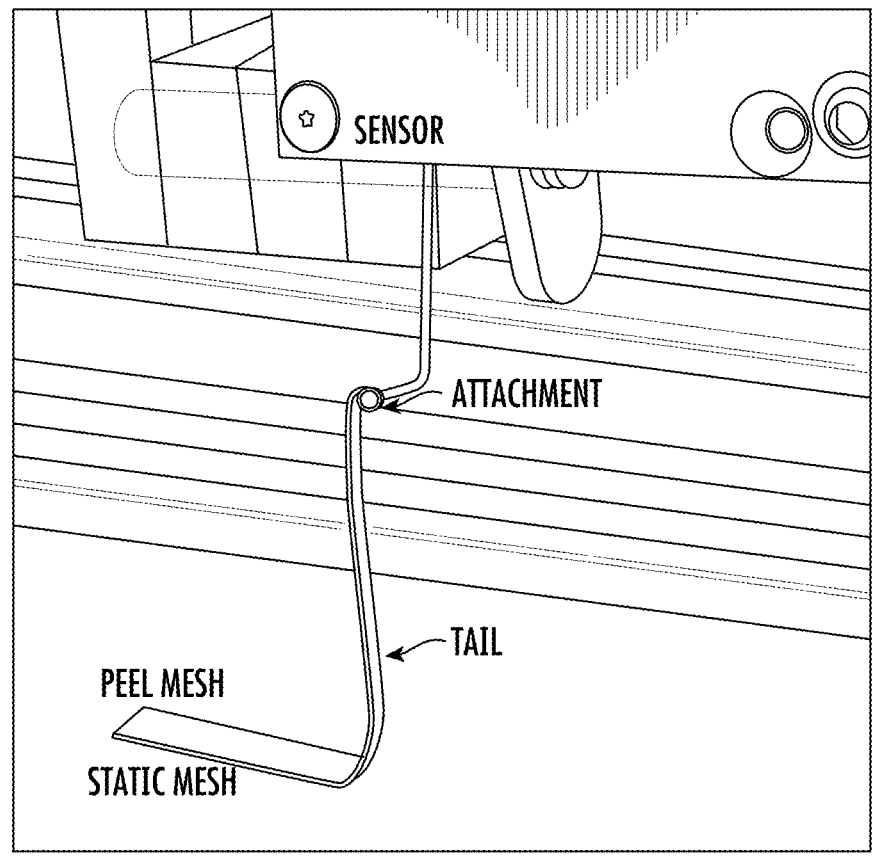
FIG. 10 is a schematic of mucoadhesion apparatus used in the Button Lab.

Mucus-film bioadhesion measurements were made using a custom-designed adhesion testing device designed for making mucus adhesion measurements (FIG. 10) (Brian Button, 2018; Goodell et al., 2019). This system utilizes a very sensitive optical sensor which was routinely calibrated by measuring the adhesive strength of calibration tape (2125 Series; 3M) peeled off of a clean steel plate using an ASTM-D3330 standard protocol for peel testers (International, 2010). A 1 $cm^2$ section of "test" film or kimwipe "control" was cut using a $CO_2$-laser and mounted to the bottom of the device probe which was on an XYZ-motorized gantry using double sided 3M tape (Goodell et al., 2019). In these studies, 5% w/v bovine submaxillary MUC5B mucin (Sigma) was used as a mimic of the MUC5B-dominate cervical mucus (Gipson et al., 2001). The mucus in these studies was positioned as stationary layer of mucus that does not detach during the bioadhesion measuring process. To do this, a mucus layer (100 μl volume) was adhered to a 1 $cm^2$ mucus-binding cellulose mesh affixed to the bottom of the measurement chamber using 3M tape (Goodell et al., 2019).

During an assay, the probe with the mounted "test" film was lowered at a rate of 1 mm/sec until it penetrated the adhered mucus layer. The film was then advanced into the mucus layer until a preload force of 200-mN was established. The preload was maintained for 60 second to allow sufficient adhesion of the film to the underlying mucus layer. After incubation, the attached film was withdrawn from the mucus at a velocity of 1 mm/s. The force exerted to remove the film sample from the mucus was measured over the duration of the study. From each experiment, the peak adhesive force and the area under force vs. distance curve (i.e., work of adhesion) were determined from the raw data using a custom MATLAB script.

Mechanical Testing

Tensile measurements were performed with a TA Instruments RSA-G2 solids analyzer in axial control mode utilizing a rectangular film clamp. All tensile measurements were performed at ambient conditions (T≈20° C., RH ~50%). Samples were cut into long rectangular strips of approximate dimensions 3×0.2 mm$^2$ (width×thickness) and affixed into the sample clamps with an initial gauge length of 40 mm. Stress-strain curves were recorded using a Hencky strain rate of 20% min$^{-1}$ until sample failure. The failure locations of each sample break were recorded, and only breaks within the middle of the sample gauge length were used for calculation of the tensile strength and elongation at break. Calculation of the Young's modulus was performed by linear regression within the linear elastic regime strain of the stress-strain curve.

In Vitro Cell Studies—Cytotoxicity Studies

The cytotoxicity of film formulations was evaluated in SK-LMS-1 vulvar cells using an ATP assay. SK-LMS-1 cells were cultured in 96-well plates in MEM media at a density of 10$^4$ cells per well and incubated for 24 h at 37° C. and 5% CO$_2$. Cells were subsequently treated with UV-sterilized mouse-sized (4 mm in diameter) placebo films (3% HMW HEC, 5% HMW HEC, 1% HPMC, 1.5% HPMC, 7% HPC and 9% HPC) and incubated for an additional 24 h at 37° C. The CellTiter-Glo® assay was performed according to the manufacturer's instructions (Promega, Madison, WI). Briefly, treated cells were allowed to incubate for 30 min at room temperature (RT). CellTiter-Glo solution was then added, cell lysis was induced for 2 min with shaking followed by a 10 min equilibration period at RT. Luminescence intensity was measured using a plate reader (BioTek Synergy 2, Winooski, VT) and the percent (%) cell viability was calculated relative to the control (cells only) luminescence intensity set as the 100%. All experiments were done in triplicate.

Cell Damage

Human leiomyosarcoma SK-LMS-1 cells (ATCC HTB-88™; Manassas, VA) were cultured in Minimum Essential Medium (MEM; Gibco, Carlsbad, CA) containing 10% fetal bovine serum (FBS; EMD Millipore Corp., Billerica, MA) and 1% penicillin streptomycin (10,000 U/mL penicillin and 10,000 ug/mL streptomycin; Gibco) in tissue culture flasks, at 37° C., 5% CO$_2$ and 95% humidity.

Cytotoxicity of film formulations was also evaluated in SK-LMS-1 vulvar cells by investigating cell damage using a lactate dehydrogenase (LDH) assay. Briefly, SK-LMS-1 cells were cultured in MEM and incubated for 24 h at 37° C. and 5% CO$_2$ as described above. UV-sterilized mouse-sized (4 mm in diameter) placebo films were placed in each well and incubated for an additional 24 h at 37° C. The Pierce LDH Cytotoxicity assay was performed according to manufacturer's instructions (ThermoScientific, Rockford, IL). Sample aliquots (150 µL) from each well (spontaneous LDH activity control, film-treated cells, and maximum LDH activity control) were transferred to a new 96-well flat-bottom plate in triplicate. Reaction Mixture was added to each well and the plate was allowed to incubate at RT for 30 min. The reaction was stopped using the kit stop solution and absorbance was measured at excitation wavelength (680 nm) and the emission wavelength (490 nm) using a plate reader (BioTek Synergy 2, Winooski, VT). Percent (%) cytotoxicity was calculated using the following equation:

% cytotoxicity=(Compound-treated LDH activity−Spontaneous LDH activity)/(Maximum LDH activity−Spontaneous LDH activity)×100. Maximum damage was induced using lysis buffer. All experiments were done in triplicate.

In Vitro Film Dissolution Studies

The dissolution rate of various film formulations was quantified using fluorescence analysis. Polymer formulations were loaded with 0.01% w/w Brilliant Blue dye. Films were casted, dried, and cut using the methods described above. Films were incubated at RT in 4 mL of a simulated vaginal fluid (SVF, 25 mM sodium acetate buffer, pH 4.2) or a phosphate buffered saline (PBS, pH 7.4) each containing 2% solutol to maintain sink conditions. At preselected time points, pictures of the dissolving films were taken and three sample aliquots (150 µL each) were collected from three different locations of the dissolution media and replaced with fresh media. Samples were placed in a 96-well plate and analyzed using an end point absorbance detection method measured at 595 nm on a BioTek Synergy 2 µlate reader.

In Vitro Drug Release Studies

Lidocaine hydrochloride (LHC) is commonly used for localized pain management and has high solubility in water (50 mg/mL) compared to lidocaine (0.41 mg/mL) (Samuel, Yalkowsky, & Jain, 2003). LHC was thus selected as the drug of choice in the present work. Homogenous solutions of drug and polymer formulations were prepared by dissolving LHC in DI water, and subsequently adding the polymer to the solution and mixing at RT overnight to allow complete dissolution of the polymer in the solution. Films were cast from the pre-made drug-polymer solutions, dried, and cut using the procedure described above. Films (n=3) were incubated in 4 mL of SVF (pH 4.2) at RT. At preset time points, sample aliquots (100 µL) were collected and replaced with 100 µL of fresh SVF. The concentration of LHC in each sample was quantified using high-performance liquid chromatography (HPLC).

High-Performance Liquid Chromatography (HPLC) Analysis.

A reverse-phase HPLC method was developed and validated to quantify the concentration of lidocaine hydrochloride (LHC) released in vitro from various thin film formulations. HPLC analyses were carried out with a Finnigan Surveyor HPLC system (Thermo Finnigan, San Jose, California, USA) equipped with a Photodiode Array (PDA) Plus Detector, auto-sampler, and LC Pump Plus. The stationary phase utilized for the analysis was a Inertsil ODS-3 column (5 µm, 4.6 A-150 mm, [GL Sciences, Torrance, CA]) maintained at 40° C. Chromatographic separation was achieved by gradient elution using a mobile phase consisting of 0.1% trifluoroacetic acid in water and acetonitrile (ACN) (H$_2$O/ACN 95:5 v/v). The flow rate was 1.0 mL/min and the total run time was 25 min for each 25 µL injection.

Example 1

Film Formulation Development and Testing

To develop a mucoadhesive thin film for treatment of vestibulodynia (VBD), three biocompatible polymers (HPC, HPMC, and HEC) were selected and tested. Polymer solutions of HPC, HPMC, and HEC were prepared with a range of polymer weight percent in DI water (Table 1). Polymer formulations were screened based on viscosity of the formulation and a qualitative assessment of the workability of their respective cast dried films. The results showed that polymer formulations with a viscosity in the range of 50-3000 cP were appropriate for film casting. Formulations that exhibited viscosity >3000 cP resulted in heterogeneous solutions due to inability of the polymer to fully dissolve in water. On the other hand, formulations with viscosity <50 cP generally produced films that were too fragile and flaky to be handled and used for this application. Based on this screening process, the best two formulations were investigated for each polymer solution (Table 1). Although 5% LMW HEC was below the ideal viscosity range, this formulation generated adequate films and was the second best formulation for LMW HEC. The following formulations were included in this study and investigated further: 1% HPMC, 1.5% HPMC, 3% HMW HEC, 5% HMW HEC, 5% LMW HEC, 7% LMW HEC, 7% HPC, and 9% HPC.

TABLE 1

Formulation screening based on rheological properties of polymer solutions. Selected formulations correspond to polymer solutions with a viscosity in the range of 50-3000 cP that can successfully be used to cast thin films. Rheological properties for solution formulations that were screened but not included in the study can be found in FIG. 10.

| Solution Formulation | Temperature (° C.) | Viscosity (cP) |
|---|---|---|
| 7% HPC | 25.00 | 192.2 |
| 9% HPC | 25.00 | 454.1 |
| 5% HEC (lmw) | 25.00 | 50.0 |
| 7% HEC (lmw) | 25.00 | 257.9 |
| 1% HPMC | 25.00 | 404.3 |
| 1.5% HPMC | 25.00 | 2435.0 |
| 3% HEC (hmw) | 25.00 | 481.7 |
| 5% HEC (hmw) | 25.00 | 3203.0 |

Example 2

In Vitro Cytotoxicity

Figure 2A:
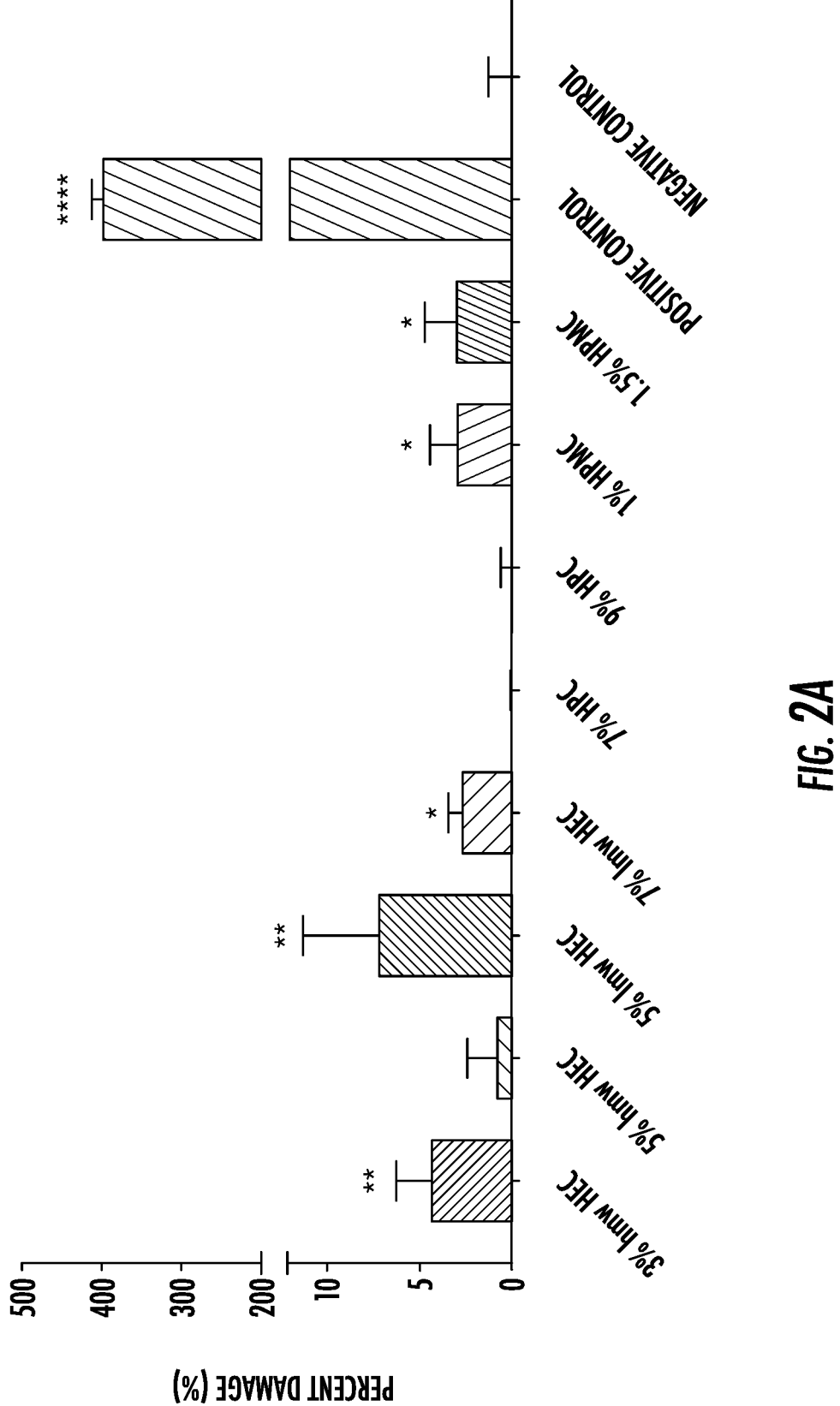
FIGS. 2A-2B show in vitro cell based assays to evaluate cytotoxicity of various film formulations in SK-LMS-1 vulvar cells.
Figure 2B:
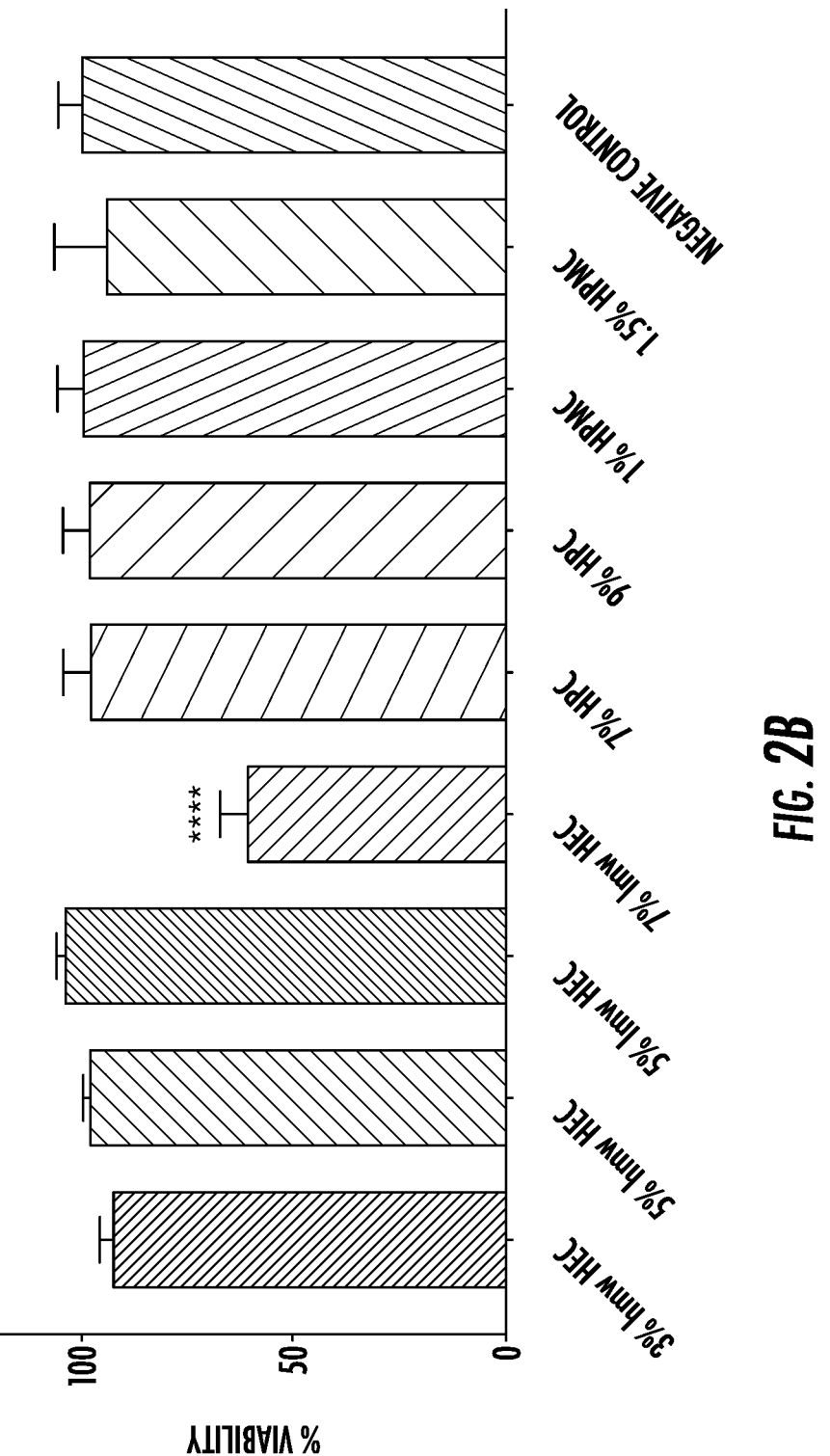
Figure 3A:
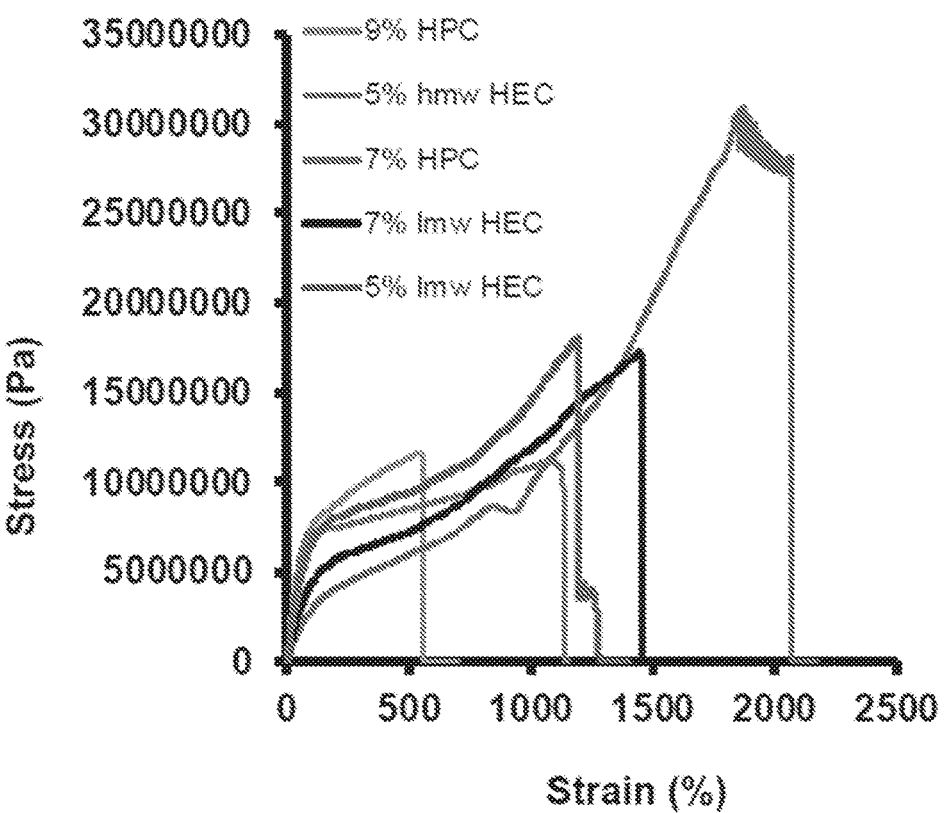
FIGS. 3A-3D show mechanical properties were examined using tensile testing for placebo films with varying properties.
Figure 3B:
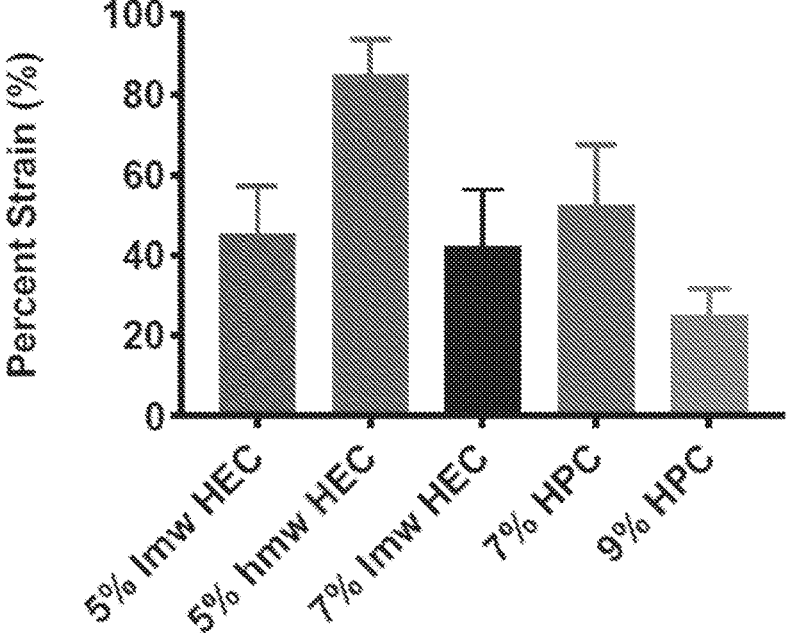
Figure 3C:
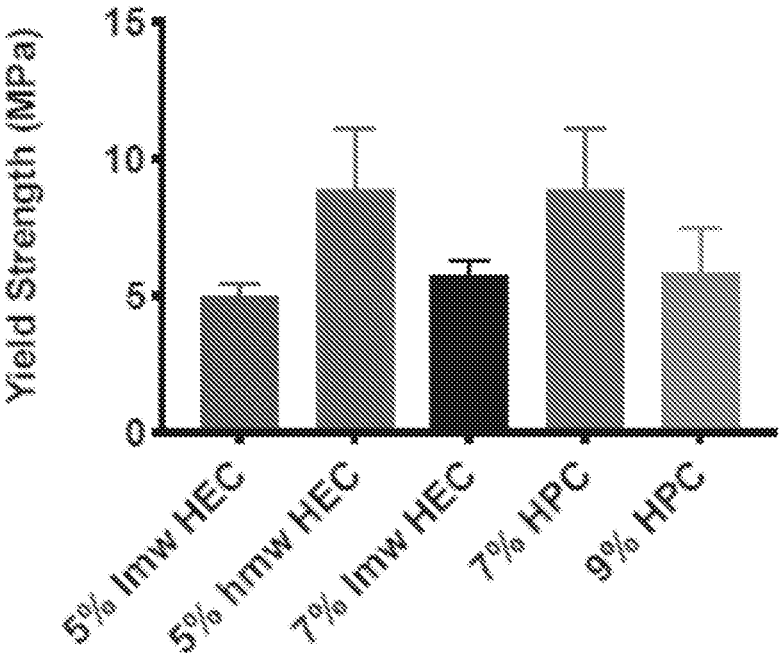
Figure 3D:
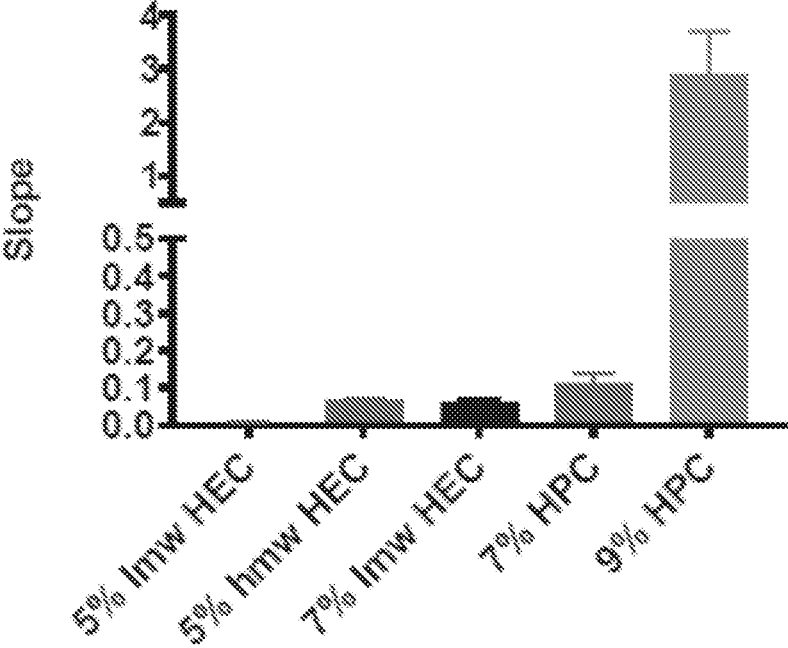
Figure 11B:
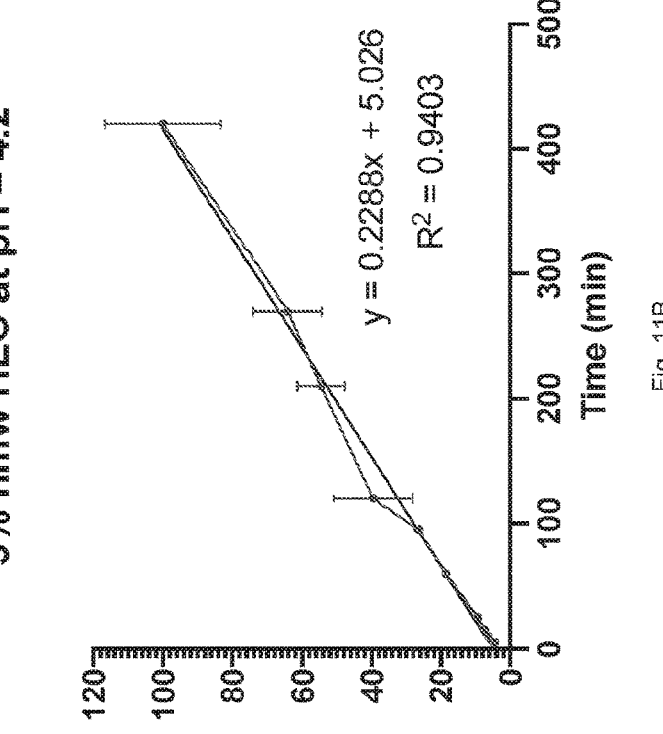
FIGS. 11A-11B show dissolution graphs for 3% and 5% hmw HEC. These films were cast at 4 mm wet thickness and dissolved in triplicate in 4 ml SVF+2% solutol. These dissolution profiles were linear, so a linear regression was performed and an equation derived to express this relationship.
Figure 11A:
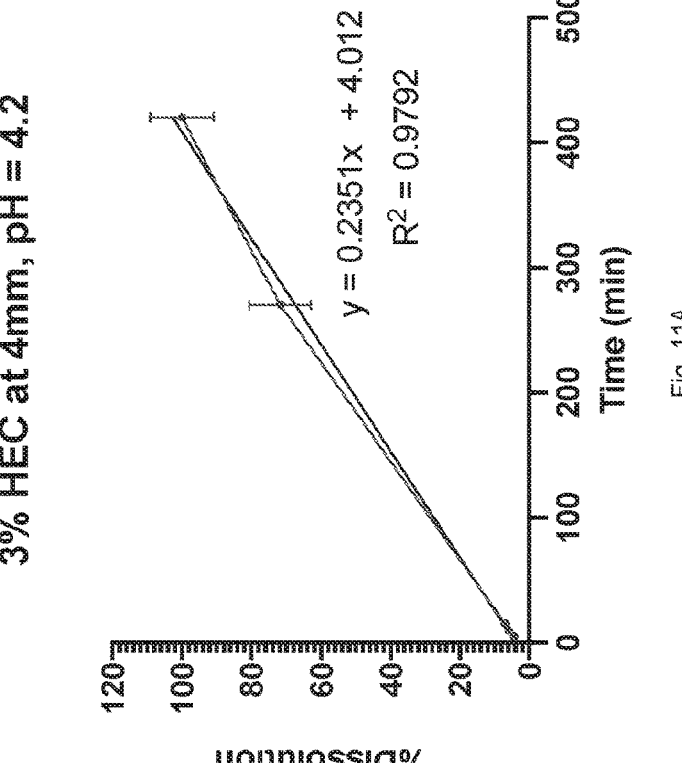

The biocompatibility of optimized film formulations was assessed for their potential use as a mucoadhesive biodissolvable film for local delivery of LHC to the vulvar tissue. Cell viability was determined using the ATP assay (CellTiter-Glo® Luminescent Cell Viability Assay) in SK-LMS vulvar cells. KS-LMS cells were cultured and incubated at 37° C. for 24 h with optimized films (4 mm circles) fabricated using a solvent-evaporation casting method. As shown in FIG. 2B, all film formulations except for 7% LMW HEC were non-toxic and showed ~100% cell viability relative to the control untreated cells. Cell viability was only ~60% for films fabricated with 7% LMW HEC (MW 90 kDa) compared to 100% cell viability for the 7% HMW HEC (MW 250 kDa). Without being bound by any particular theory or mechanism of action, the difference in cell viability for the 90 kDa HEC films could be attributed to its lower molecular weight which can lead to faster dissolution upon incubation with cells over 24 h and potential change in osmolarity and cell viability. However, the dissolution rate of LMW HEC and HMW HEC was relatively the same and both fully dissolved within ~3.5 h upon incubation in SVF (FIGS. 11A-11B).

Example 3

Cell Damage Studies

The biocompatibility of optimized films was also assessed by quantifying cell damage in SK-LMS-1 vulvar cells using a lactate dehydrogenase (LDH) cytotoxicity assay (Thermo-Scientific). Lysed cells were used as a positive control and showed significant damage (~400%) relative to the control untreated cells (FIG. 2A). All film formulations showed no or minimum cell damage effects ranging from 0-7 relative to the control untreated cells.

Example 4

Mechanical Testing

The elastic properties of thin films is an important aspect for their ability to be handled and applied to the vulvar area. The resistance and elasticity of films was measured with a TA Instruments RSA-G2 solids analyzer in axial control mode at ambient temperature. To evaluate the mechanical testing data, four correlations were examined using an unpaired two-tailed t-test to compare the difference in Young's modulus, yield strength, and strain at fracture. The four correlations of interest were: the effect of polymer type, effect of polymer content, effect of drug loading, and the effect of molecular weight on film mechanical properties. The effect of polymer type was determined by comparing the properties of two formulations containing the same polymer weight percent: 7% LMW HEC (n=3) and 7% HPC (n=3). In this case the polymer content and testing parameters were kept constant with the only variable being the polymer type (LMW HEC vs. HPC). It was found that the Young's modulus was significantly different (p<0.05), the yield strength was significantly different (p<0.05), and the strain at fracture was not significantly different (p=0.35) (FIG. 3).

To evaluate the effect of polymer content, 9% HPC (n=3) and 7% HPC (n=3) were compared keeping all other parameters constant. The Young's modulus was found to be significantly different (p<0.05), the yield strength was not significantly different (p=0.07), and the strain at fracture was significantly different (p<0.05).

The effect of drug presence on film mechanical properties was also investigated by comparing 9% HPC placebo films (n=3) with 9% HPC films loaded with 0.43 mg LHC/mg film (n=3). Results showed that the Young's modulus was significantly different (p<0.05), the yield strength was significantly different (p<0.05), and the strain at fracture was also significantly different (p<0.05).

Finally, the effect of polymer molecular weight on film mechanical properties was determined by comparing 5% HMW and 5% LMW HEC placebo films. The Young's modulus was significantly different (p<0.05), the yield strength was statistically different (p<0.05), and the strain at fracture was also significantly different (p<0.05) (FIG. 3 and Table 2 below). HMW HEC films were more flexible than LMW HEC as reflected by a significantly higher Young's modulus and were less flaky and less brittle to the touch compared to LMW HEC films. Moreover, given that HMW HEC and LMW HEC both exhibited similar dissolution rates, only HMW HEC was further investigated in subsequent studies.

TABLE 2

Mechanical properties were examined using tensile testing for placebo
films with varying properties, including percent strain at fracture,
ultimate strength, yield strength and Young's Modulus.

| Solution Formulation | Young's Modulus (MPa) | Yield Strength (MPa) | Ultimate Strength (MPa) | Percent Strain (%) |
|---|---|---|---|---|
| 7% HPC | 0.113 ± 0.03 | 5.76 ± 0.51 | 11.44 ± 1.04 | 52.42 ± 15.42 |
| 9% HPC | 2.92 ± 0.78 | 5.85 ± 1.57 | 12.65 ± 2.53 | 25.12 ± 6.67 |
| 5% hmw HEC | 0.007 ± 0.001 | 8.84 ± 2.24 | 25.87 ± 6.24 | 85.04 ± 8.84 |
| 7% lmw HEC | 0.059 ± 0.011 | 4.33 ± 0.377 | 12.61 ± 3.45 | 42.40 ± 14.18 |
| 5% lmw HEC | 0.067 ± 0.006 | 4.92 ± 0.537 | 16.38 ± 3.91 | 45.47 ± 11.90 |
| 7% HPC | 0.113 ± 0.03 | 5.76 ± 0.51 | 11.44 ± 1.04 | 52.42 ± 15.42 |
| 9% HPC | 2.92 ± 0.78 | 5.85 ± 1.57 | 12.65 ± 2.53 | 25.12 ± 6.67 |

Example 5

Correlation Between Casting Parameters and Film Properties

Figure 4:
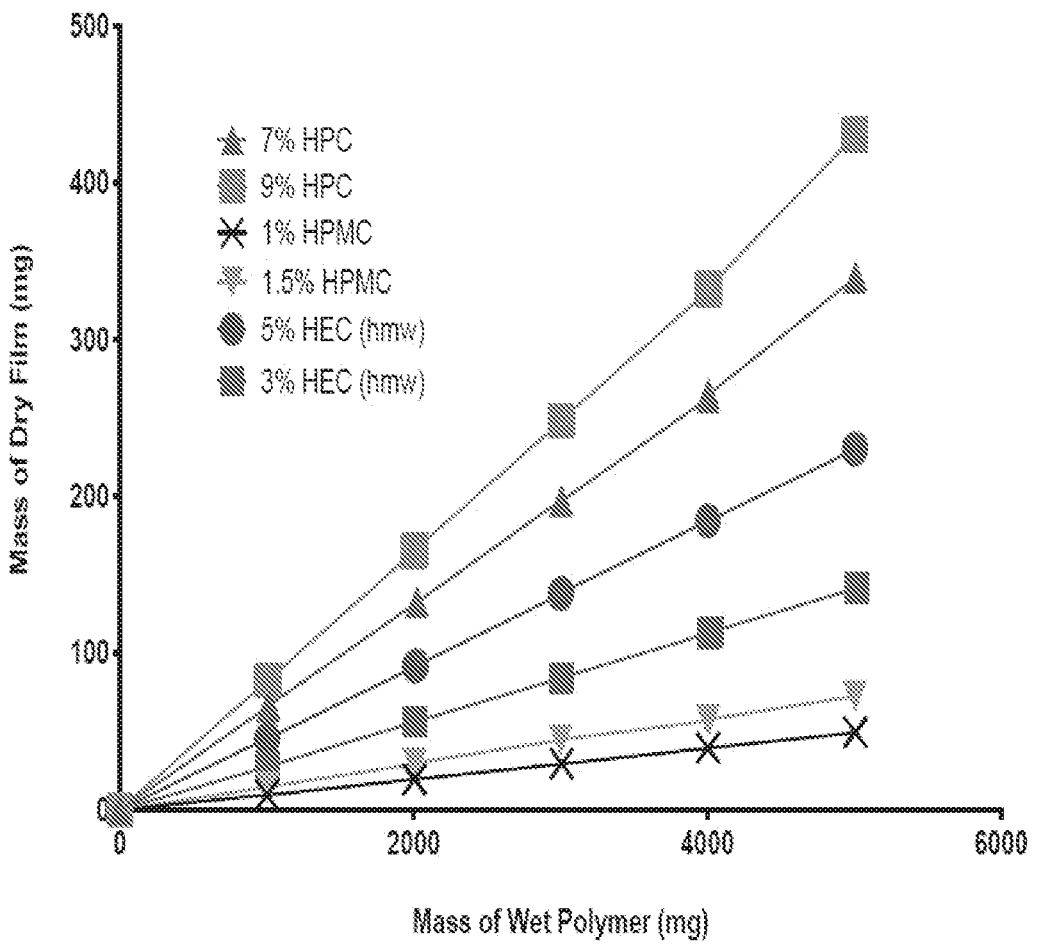
FIG. 4 shows correlation between casting parameters and final film properties. A correlation between starting wet weight of polymer solution and final dry dried film casted was determined. The linear relationship between wet polymer solution and dry film masses is graphed, and an equation to summarize the relationship was derived. This equation was validated by choosing two target dry film weights and calculating the required wet polymer to achieve the target dry film. The analytical results are shown in the table. The accuracy of these wet to dry equations is almost 100% for each polymer type.
Figure 5A:
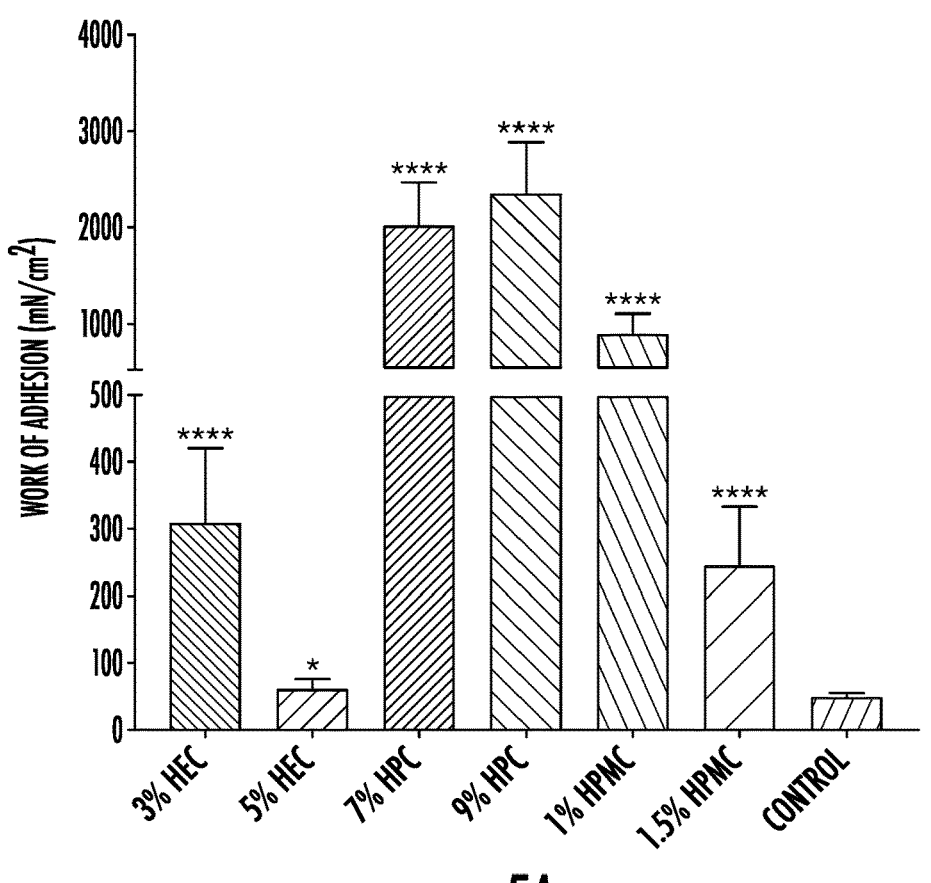
FIGS. 5A and 5B show peel test of mucus-film adhesive strength.
Figure 5B:
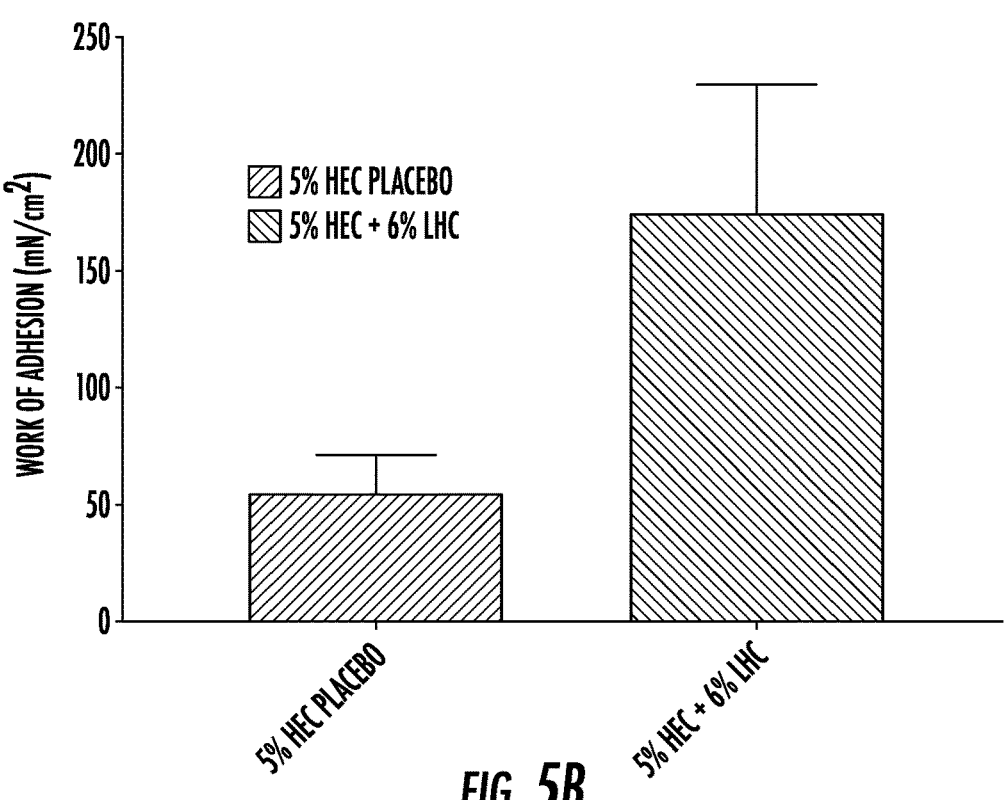
Figure 12:
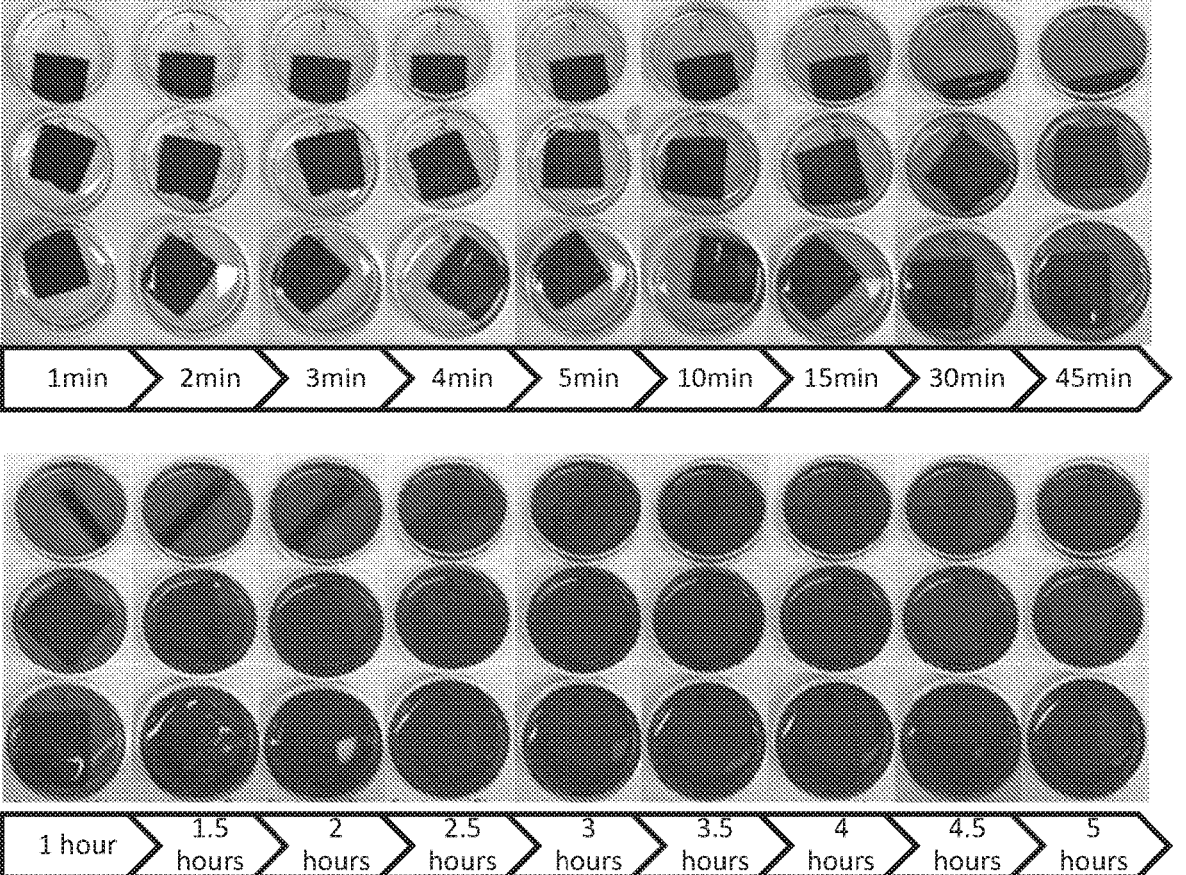
FIG. 12 shows 5% HEC dissolution study images per time point. These images show the dissolution of the blue film overtime and n=1 demonstrates the 'burrito' effect that the HEC films sometime exhibit when exposed to liquid.
Figure 13A:
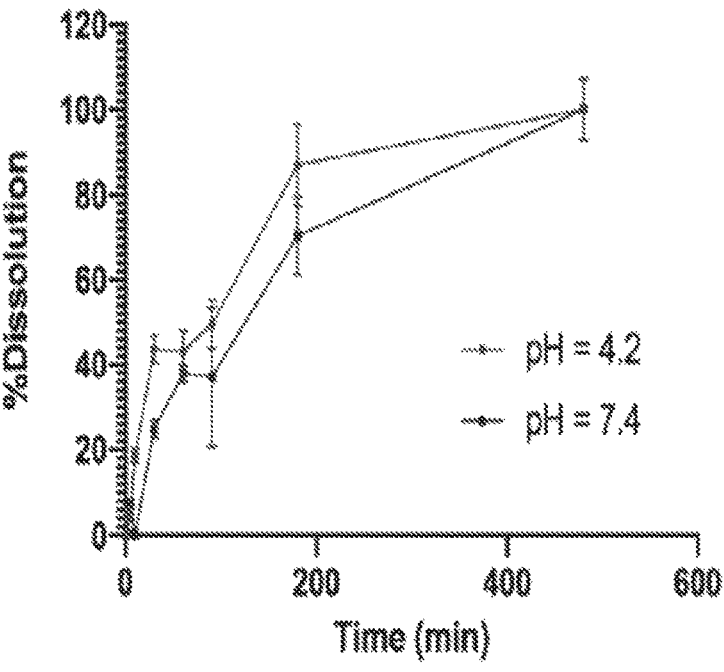
FIGS. 13A-13F show triplicate dissolution studies effect of pH in dissolution media. The effect of pH is represented here with films dissolved in 4 ml of SVF+2% solutol (pH=4.2) or 4 ml of PBS+2% solutol (pH=7.4).
Figure 13B:
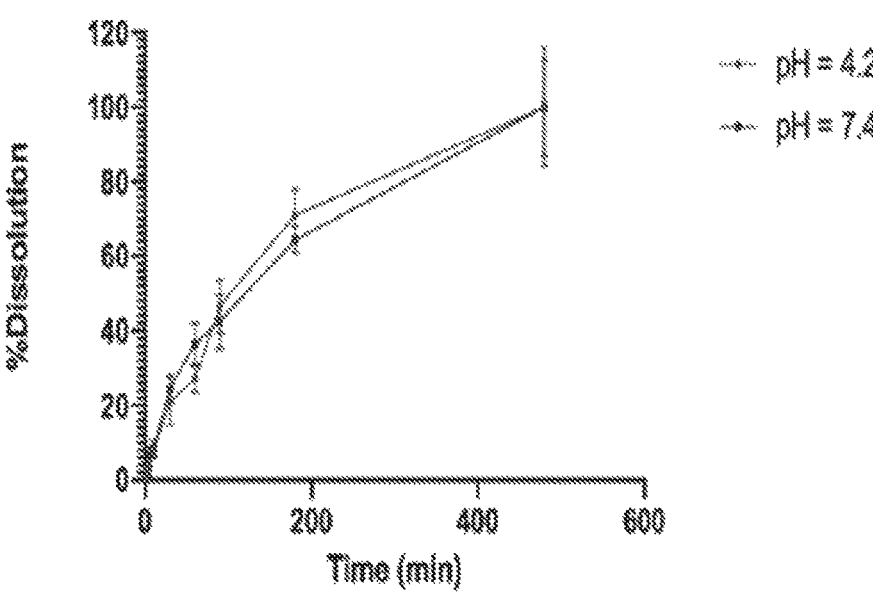
Figure 13C:
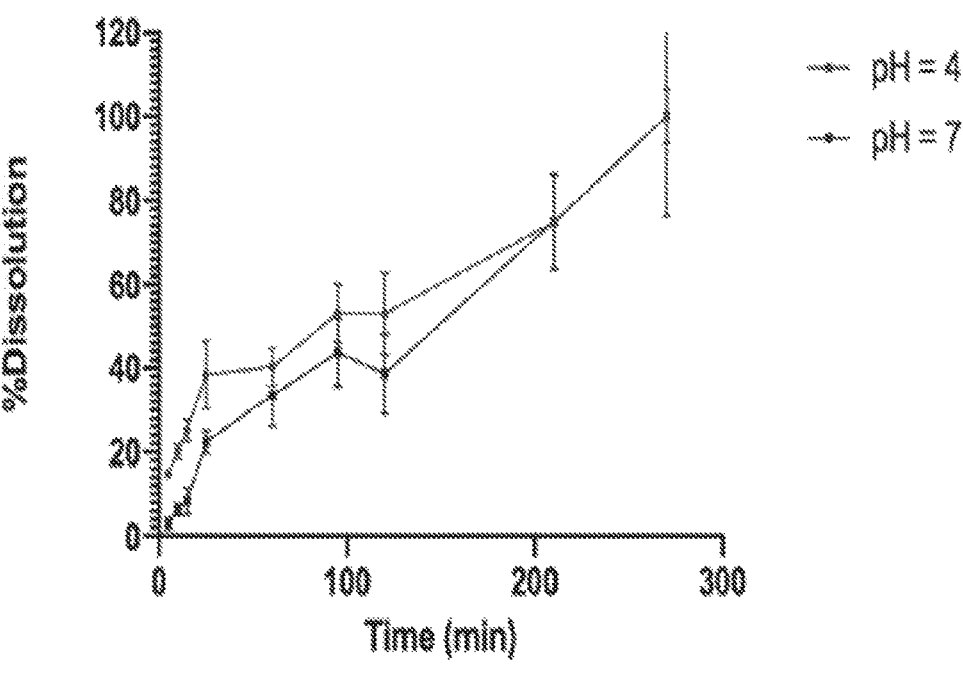
Figure 13D:
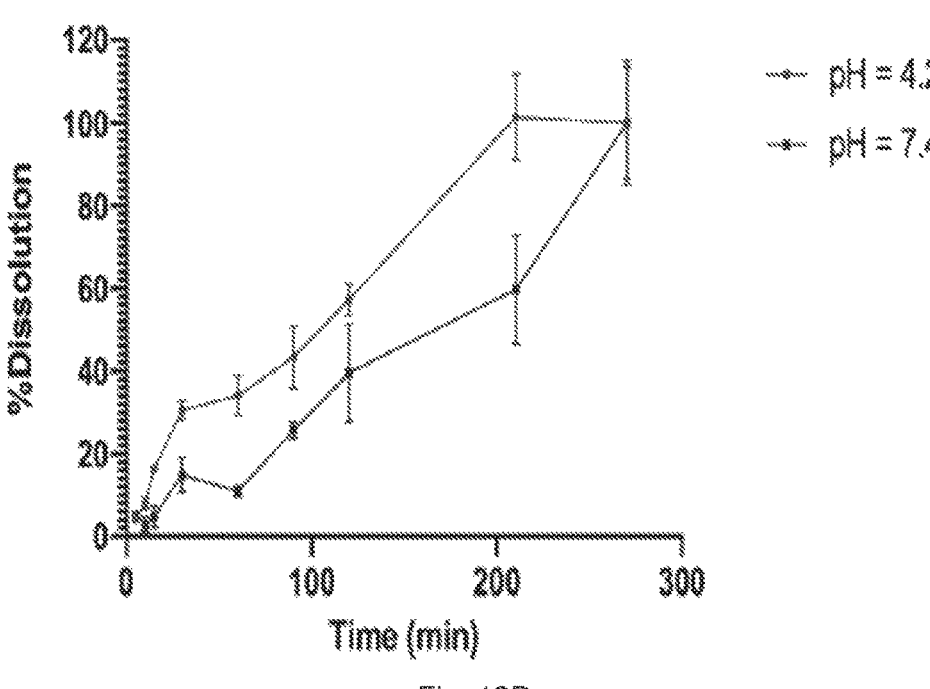
Figure 13E:
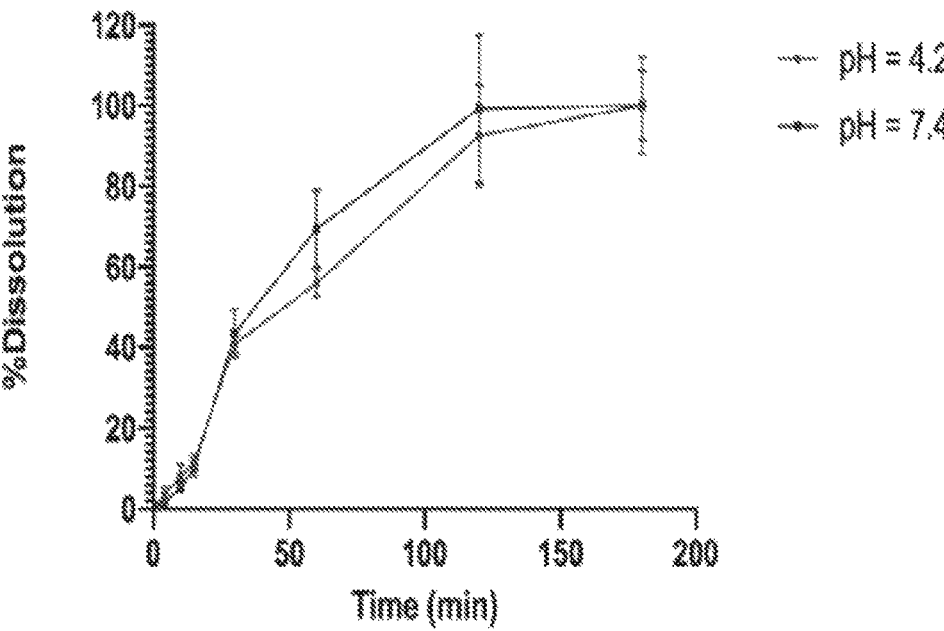
Figure 13F:
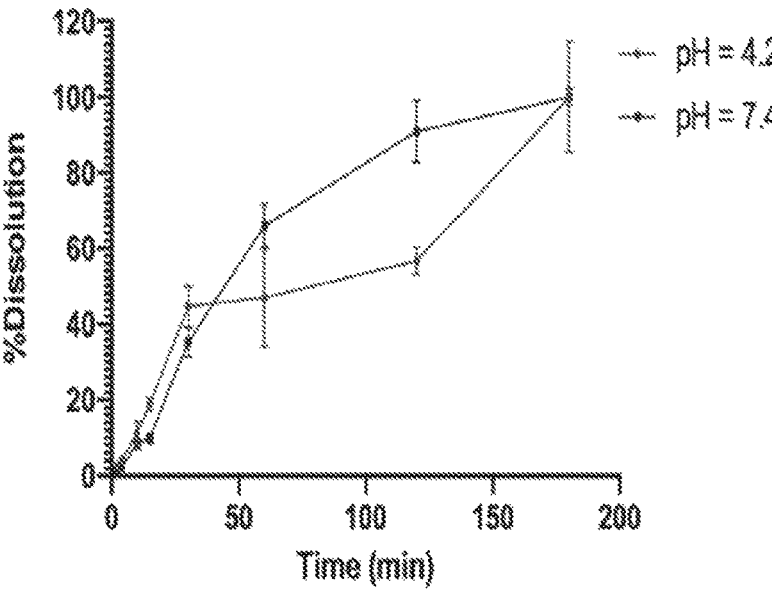
Figure 14A:
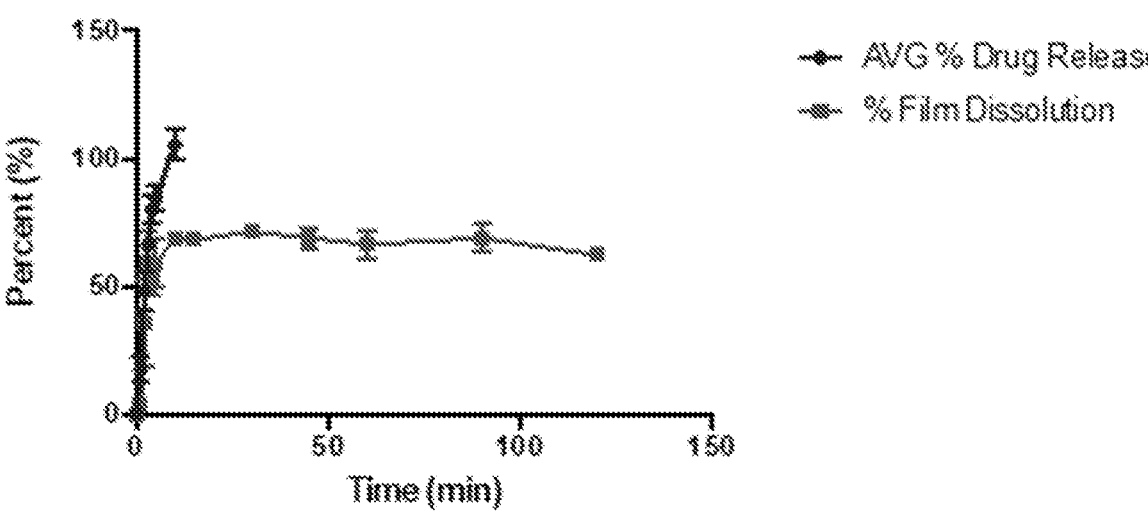
FIGS. 14A-14L show comparisons of the dissolution rate versus drug release profiles for each formulation. These studies were performed in 4 ml SVF+2% solutol. All the formulations demonstrate that the drug release is not dissolution controlled, but that the LHC diffuses out more quickly than the film dissolves.
Figure 14B:
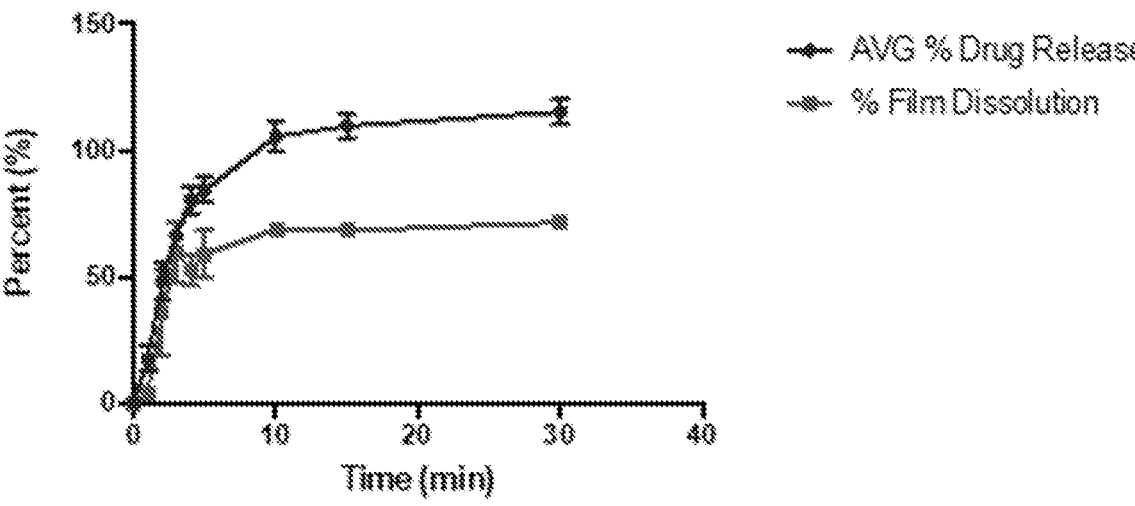
Figure 14C:
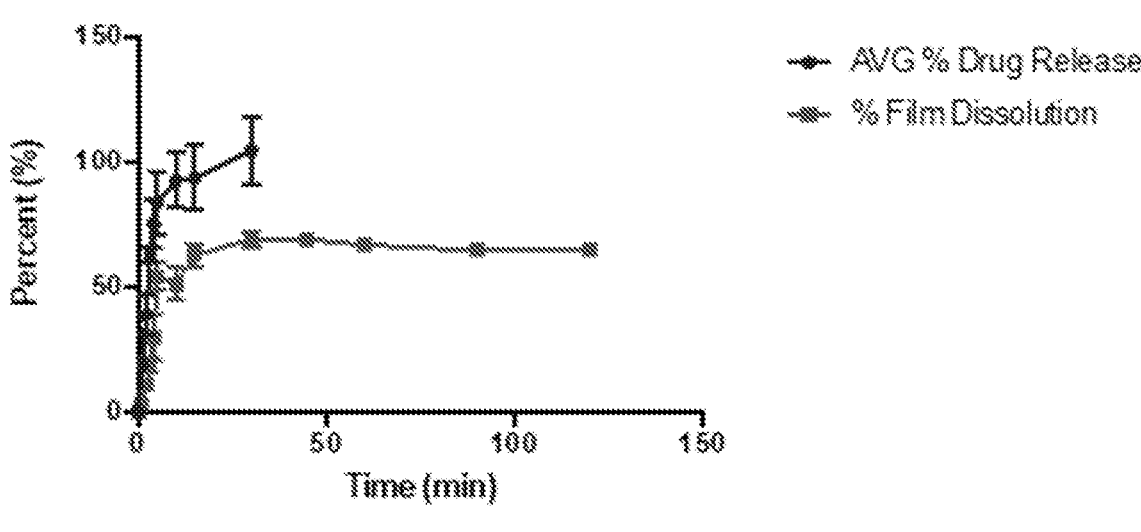
Figure 14D:
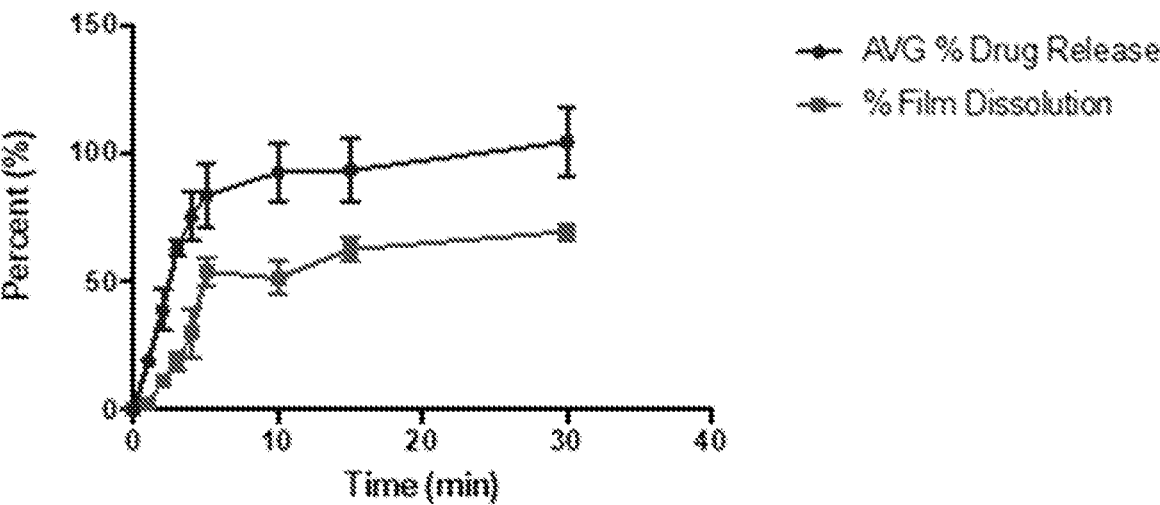
Figure 14E:
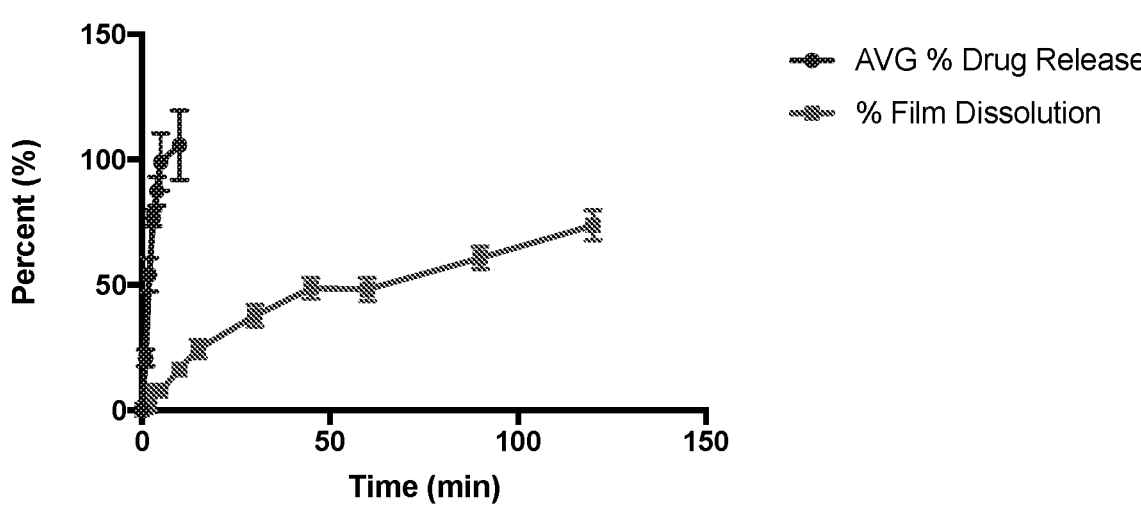
Figure 14F:
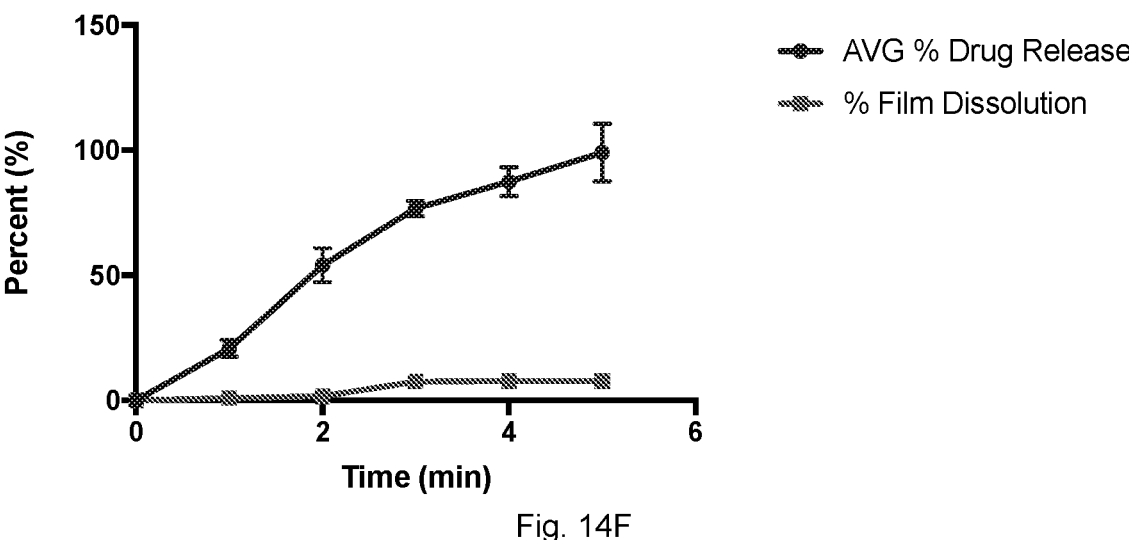
Figure 14G:
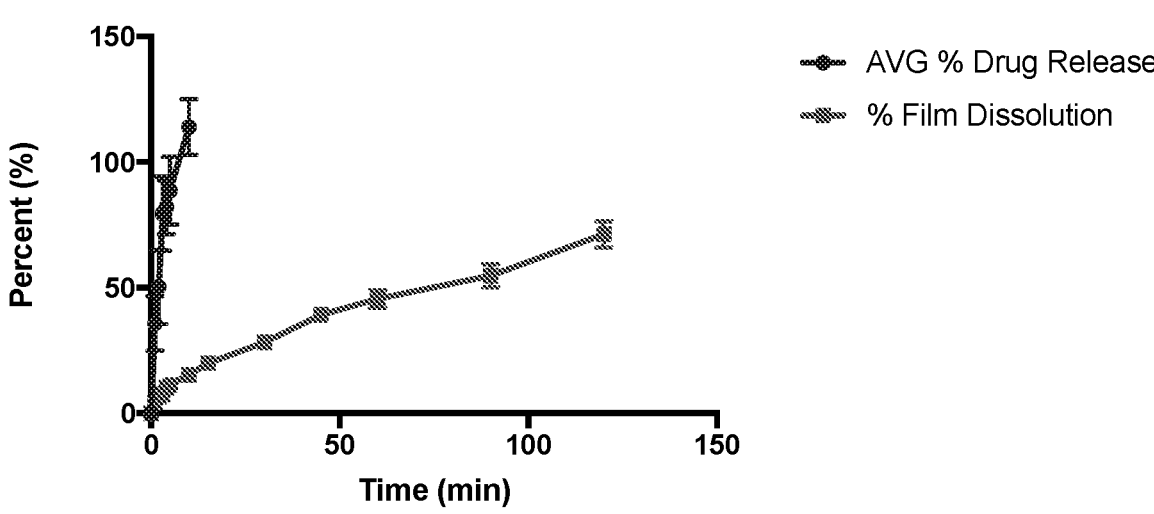
Figure 14H:
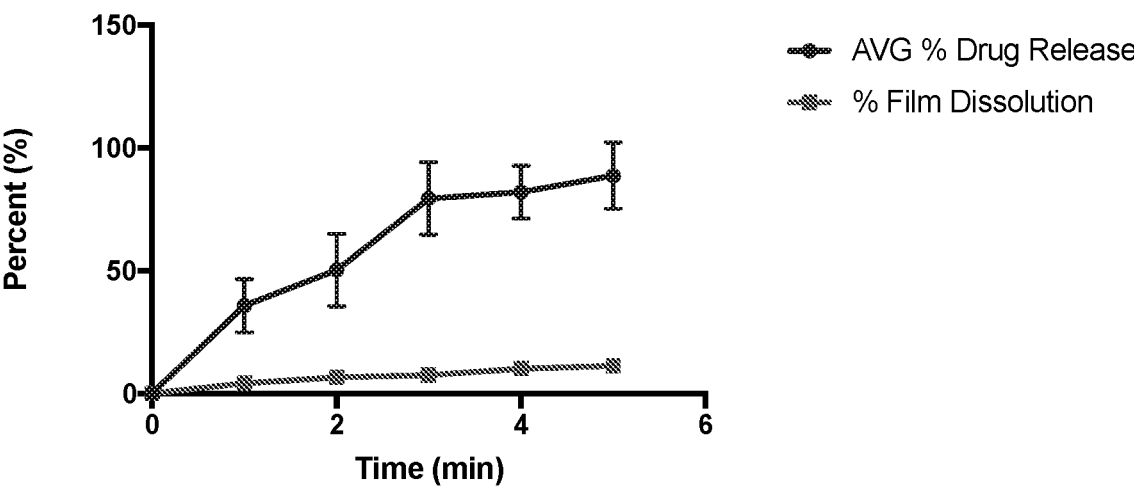
Figure 14I:
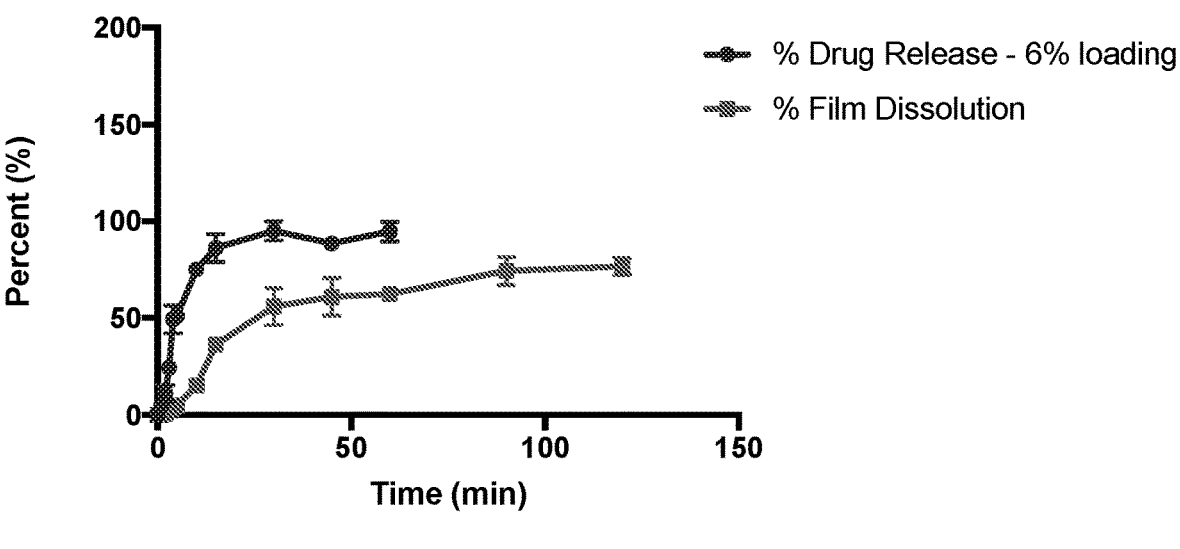
Figure 14J:
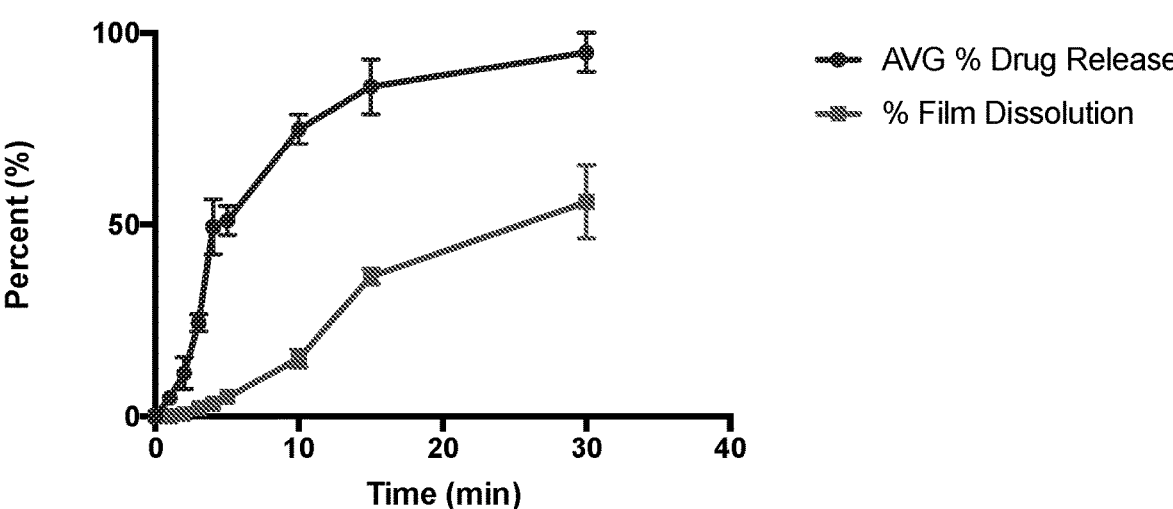
Figure 14K:
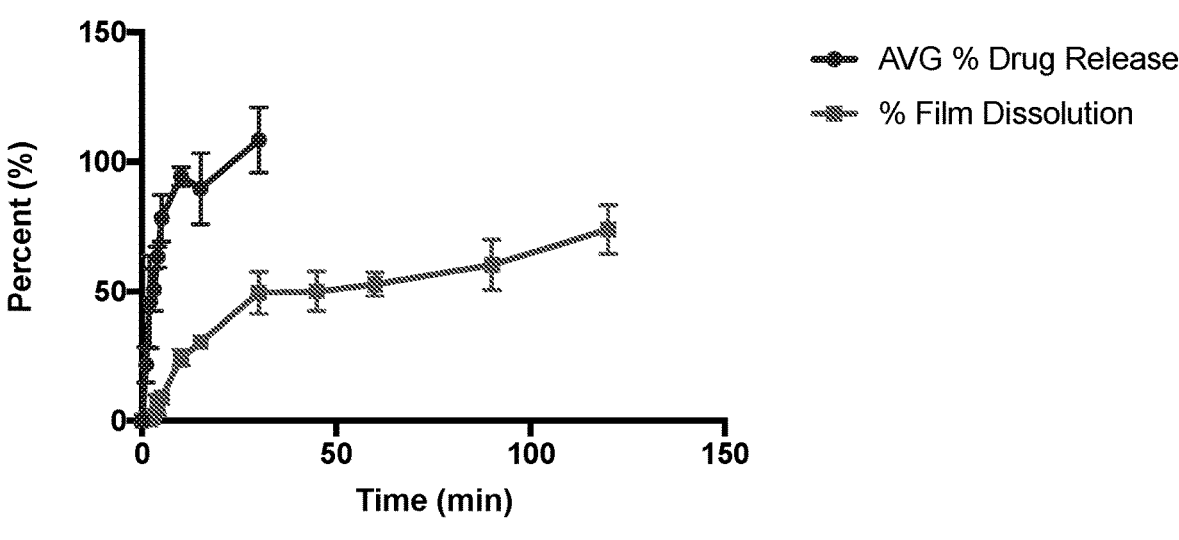
Figure 14L:
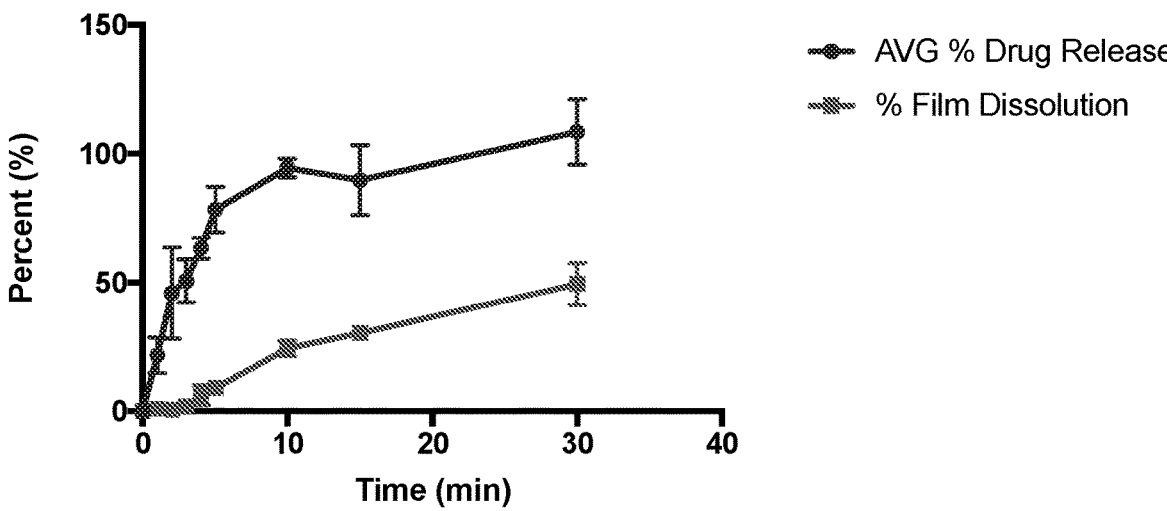

To develop an understanding of the effect of casting parameters on film properties, the correlation between the casting thickness of polymer solutions (wet thickness) and final dried film thickness and weight were investigated. To determine the ratio between wet casted polymer solutions and their respective dried thin films, films were casted using predetermined polymer solution weights (1, 2, 3, 4, and 5 g) in triplicate. After drying at 40° C. for 8 h, the final weights of films fabricated were recorded and used to calculate percent mass loss (FIG. 12) relative to each starting polymer solution weight. As shown in FIG. 4 and Table 3 there was a linear correlation between the initial polymer solution mass and final weight of dried film. The resulting linear regression equations derived from these correlations between wet polymer solution and dry film weights can be used to predetermine the weight of polymer solution needed to cast a film at a specific thickness.

highest adhesive forces and exceed the range of sensor detection at some points as reflected by the large error bars. The peak force was ~52-fold and ~40-fold higher than the control for the 9% HPC and 7% HPC, respectively. For both HEC and HPMC, increasing the polymer concentration in the solution resulted in a decrease in peak force. For HEC, increasing the polymer content from 3% to 5% resulted in a 5.6-fold reduction in peak force (308.18 vs. 54.62 mN/cm$^2$; unpaired two-tailed t-test; p<0.05). Similarly for HPMC, increasing the polymer content from 1% to 1.5% resulted in a 3.5-fold decrease in peak force (865.84 vs. 243.65 mN/cm$^2$; unpaired two-tailed t-test; p<0.05). The effect of drug loading on mucoadhesive properties was determined by comparing a 5% HEC placebo film to a drug loaded 5% HEC film. Results in FIG. 5B show that the peak force was 3.2-fold higher for the drug loaded film compared to the placebo film (unpaired two-tailed t-test; p<0.05). The increase in mucoadhesive properties in the presence of lidocaine hydrochloride (LHC) could be attributed to greater electrostatic interactions and hydrogen bonding between the film and mucin promoted by the presence of LHC.

TABLE 3

Correlation between casting parameters and final film properties.

| Solution Formulation | Wet to Dry Equation | R$^2$ | Target Dry Film Weight (mg) | Analytical Dry Film Weight (mg) | % Accuracy |
|---|---|---|---|---|---|
| 7% HPC | y = 0.046x | 1.0000 | 100 | 99.8 | 99.8 |
| | | | 300 | 301.7 | 99.4 |
| 9% HPC | y = 0.0842x | 0.9996 | 120 | 117.9 | 98.3 |
| | | | 390 | 386.4 | 99.1 |
| 1% HPMC | y = 0.0099x | 0.9999 | 15 | 14.3 | 95.3 |
| | | | 35 | 34.7 | 99.1 |
| 1.5% HPMC | y = 0.0145x | 0.9997 | 20 | 19.7 | 98.5 |
| | | | 50 | 50.3 | 99.4 |
| 3% HEC (hmw) | y = 0.0661x | 0.9996 | 40 | 39.3 | 98.3 |
| | | | 100 | 99.5 | 99.5 |
| 5% HEC (hmw) | y = 0.0282x | 1.0000 | 70 | 70.0 | 100 |
| | | | 200 | 202.4 | 98.8 |

Example 6

Mucoadhesion Studies

Film mucoadhesive properties were evaluated by tensile measurement on dry films fabricated with a range of polymer solutions. The results from tensile force and work of adhesion are illustrated in FIG. 5A and Table 4. All film formulations exhibited mucoadhesive properties relative to the control, with HPC having the highest mucoadhesive properties compared to HPMC and HEC. HPC had the

TABLE 4

Mucoadhesive properties of various placebo films
(1 cm$^2$ square) compared to control (1 cm$^2$ square kimwipe)
measured as the force (mN/cm$^2$) exerted to remove
the film sample from the mucus surface.

| Solution Formulation | Average Work of Adhesion (mN/cm$^2$) | SD |
|---|---|---|
| 3% HEC (hmw) | 308.18 | 113.06 |
| 5% HEC (hmw) | 61.44 | 14.85 |
| 7% HPC | 2009.64 | 448.95 |

TABLE 4-continued

Mucoadhesive properties of various placebo films
(1 cm² square) compared to control (1 cm² square kimwipe)
measured as the force (mN/cm²) exerted to remove
the film sample from the mucus surface.

| Solution Formulation | Average Work of Adhesion (mN/cm²) | SD |
|---|---|---|
| 9% HPC | 2349.73 | 526.35 |
| 1% HPMC | 865.84 | 204.90 |
| 1.5% HPMC | 243.65 | 88.65 |
| Control | 46.99 | 9.87 |

All measurements were done in triplicate. Statistical analyses were done using an unpaired two-tailed t-test, and statistical significance is shown as: P≤30.05 *, P≤0.01 , P≤0.001 *, P≤0.0001 ****.

Example 7

In Vitro Dissolution Studies

The dissolution rate and LHC release kinetics from fast dissolving films were determined by fluorescence analysis and HPLC analysis respectively (FIGS. 6 and 7). First, the parameters that influenced the dissolution rate of the polymeric films were investigated. The top box in FIG. 6 highlights the parameters that had no effect on the dissolution rate, and the bottom box highlights the parameters that had an effect on dissolution rate. Representative graphs are shown for each parameter investigated, although these studies were done for all formulations (FIGS. 13A-13F).

Figure 6A:
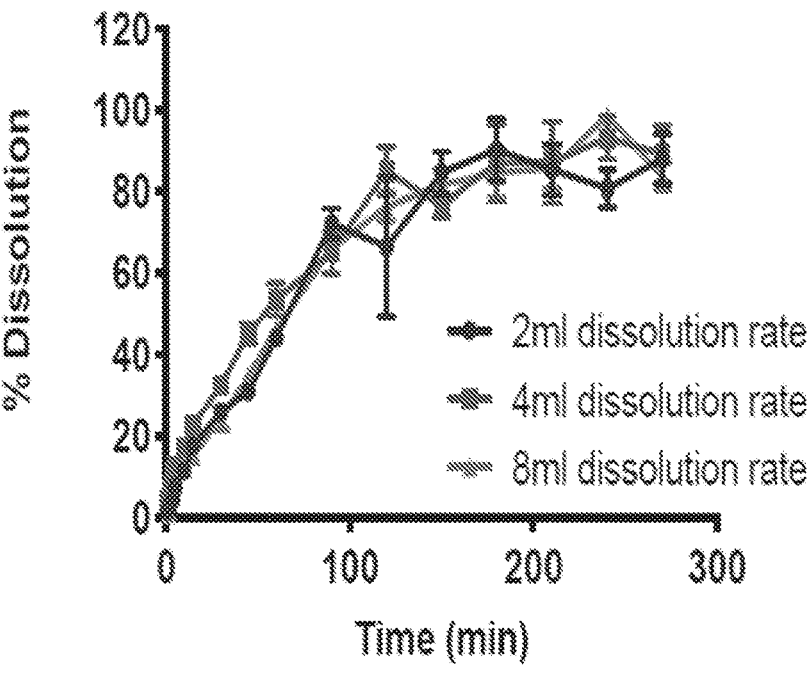
FIGS. 6A-6G show in vitro film dissolution studies. Films containing brilliant blue dye (0.01% w/w) were prepared and dissolution rate was quantified by spectrophotometry analysis.
Figure 6B:
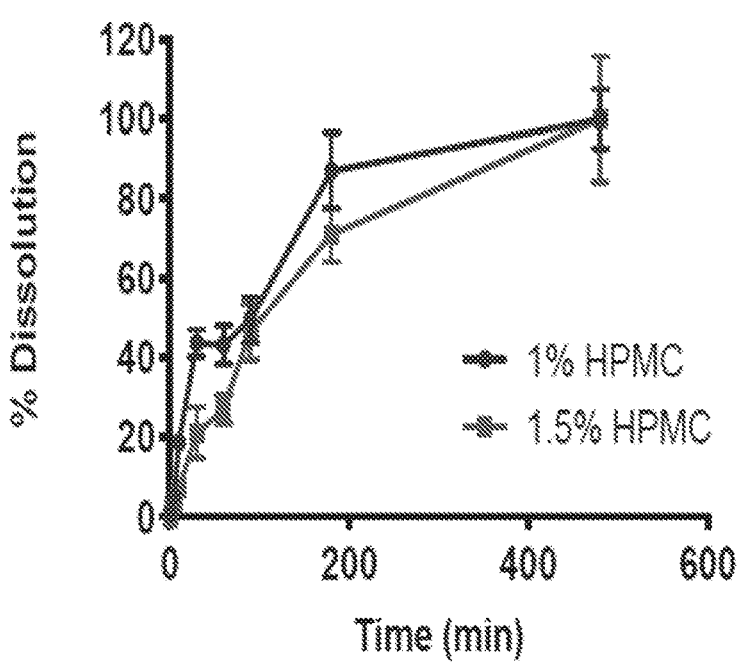
Figure 6C:
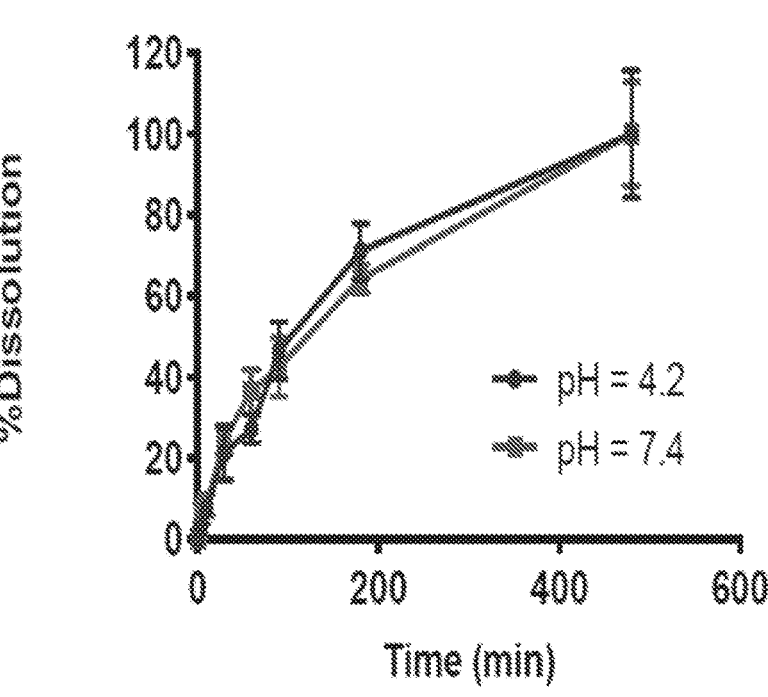
Figure 6D:
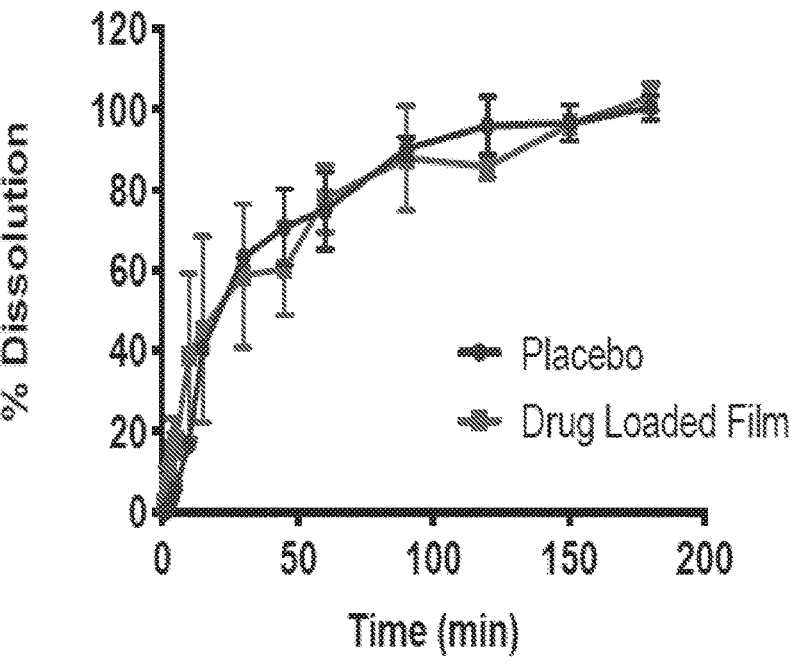

Given that the average vaginal discharge within 24 h ranges between 2-5 mL (Sobel, 2016), the effect of dissolution media volume (2, 4, 8 mL) on the rate of film dissolution was investigated. As shown in FIG. 6A the rate of film dissolution was independent of media volume with no statistical difference in percent dissolution across all media volumes. The pH of the vulva ranges from that of the vagina (4.2) to the pH of the skin (7.4), so the effect of the dissolution media pH on dissolution rate was explored. The presence of drug (placebo vs LHC loaded) and polymer content (1% vs 1.5% HPMC) were also investigated. As shown in FIG. 6A-D, these parameters did not have an effect on film dissolution rate.

Figure 6E:
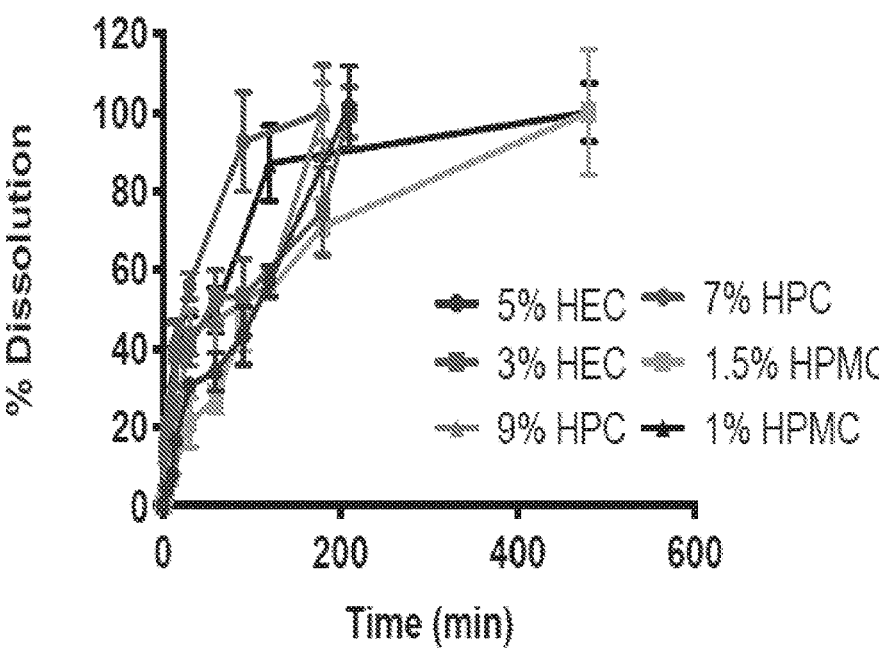
Figure 6F:
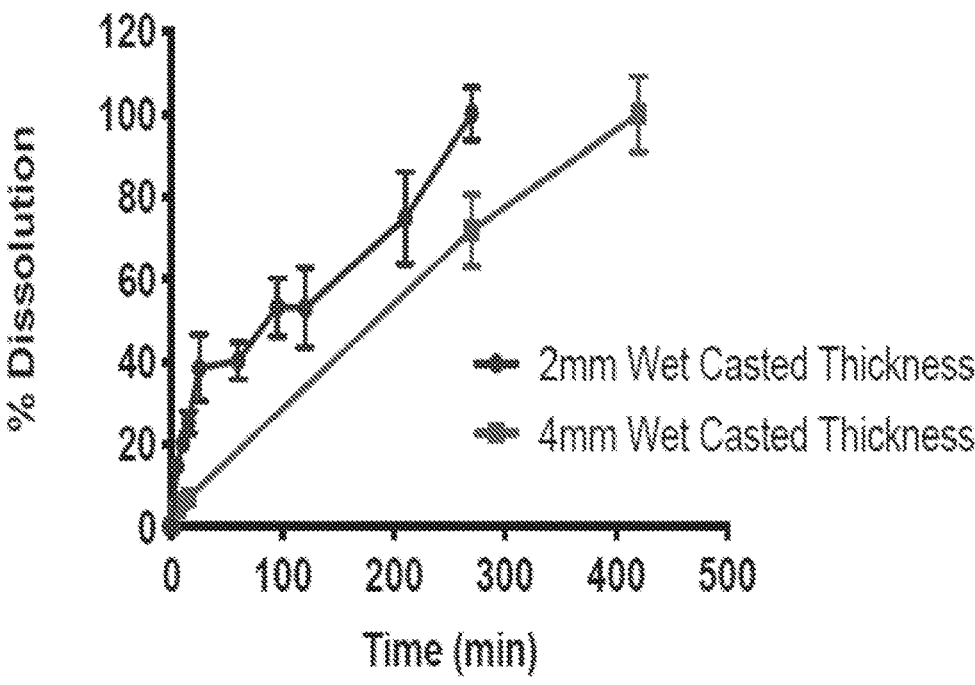
Figure 6G:
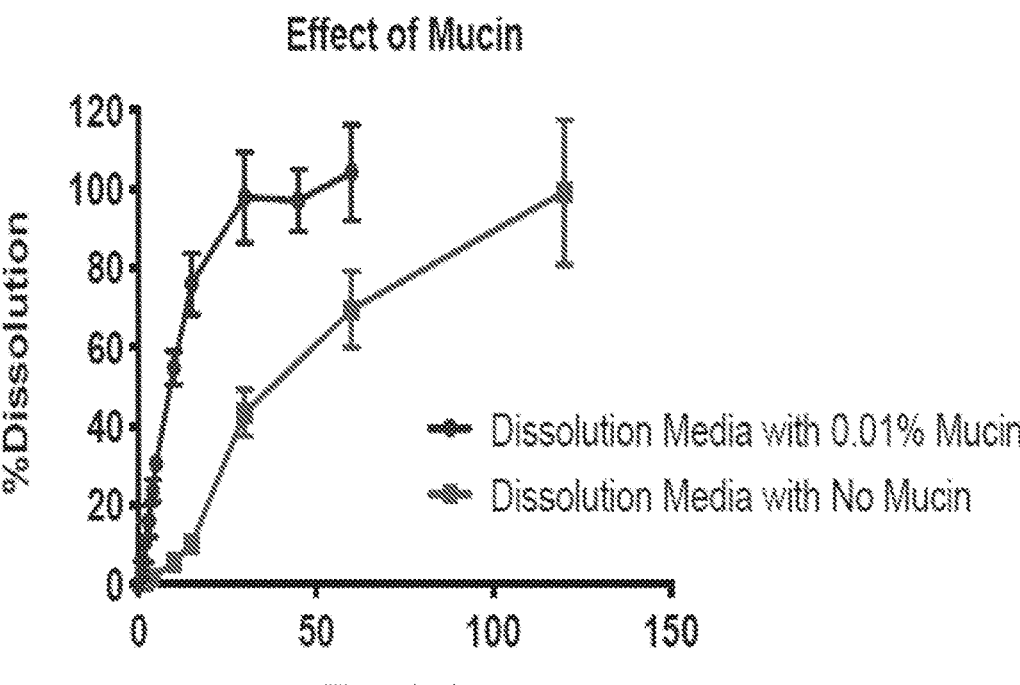

The parameters that were found to have an effect on dissolution rate were: polymer type, wet casting thickness, and the presence of mucin. Three polymers were investigated (HEC, HPC and HPMC) to compare dissolution rates. These polymers were selected to develop a fast dissolving mucoadhesive film for local delivery of LHC to the vulva. As shown in FIG. 6E, films prepared with HPMC (1% and 1.5% w/w HPMC) dissolved the slowest reaching 100% dissolution in 8 h compared to HEC and HPC films reaching 100% dissolution in 4.7 h and 3 h respectively. The effect of wet casting thickness on film dissolution rate was investigated by casting 3% HEC films at 2 mm and 4 mm wet casting thickness, respectively. Results showed that films casted at 2 mm dissolved faster and reached 100% dissolution compared to ~72% dissolution when casted at 4 mm in 4.5 h (FIG. 6F). Additionally, the effect of mucin on film dissolution rate was investigated. As shown in FIG. 6G, in the presence of mucin (4 mL SVF+0.01% w/w) 7% HPC placebo film dissolved faster and reached 100% dissolution in 60 min compared to 120 minutes in the absence of mucin.

Example 8

In Vitro Drug Release

Figure 7A:
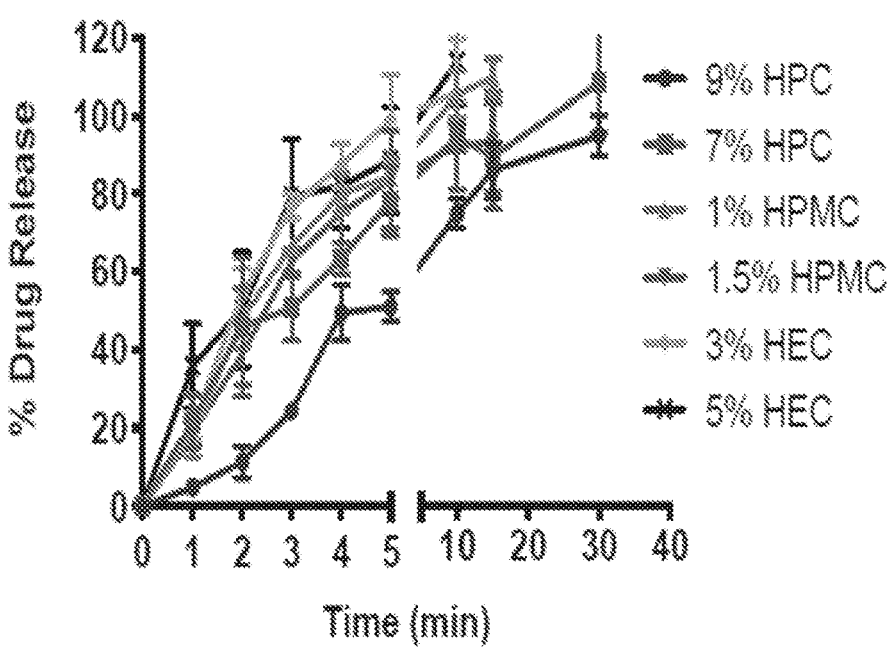
FIGS. 7A-7D show in vitro drug release studies were carried out by incubating films (n=3) in SVF+2% solutol (4 mL) at RT.

A number of factors can influence drug release from a dosage form like a thin film. These factors include film properties (polymer type, film thickness, surface area), drug physical/chemical properties, and drug loading. To achieve a translational dose, LHC was loaded at 50 mg/film, a dose equivalent to the current standard of care treatment with 5% lidocaine ointment. Film composition and polymer type had a significant effect on LHC release kinetics. Results showed that when loaded at a constant concentration across polymer types (6% LHC in solution formulation) LHC released fastest from HEC films (3% and 5% HEC) and reached 100% release in 5 min. This release was ~3-fold and ~1.5-fold faster within 5 min for HEC films compared to HPC (~29% LHC release) and HPMC (~56% LHC release) films respectively (FIG. 7A). Results in FIG. 7A show that drug release from the various film formulations mainly occurred via drug diffusion from the film and reached 100% release prior to complete (100%) film dissolution.

Figure 7B:
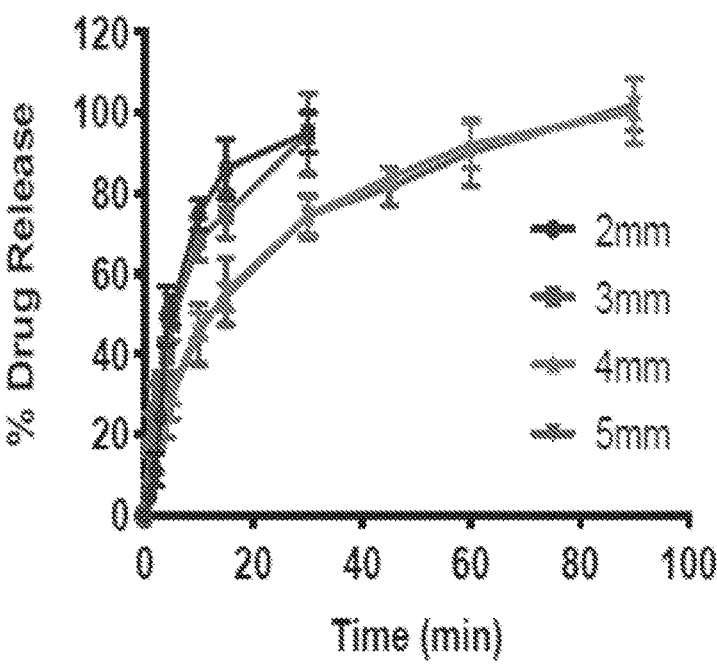

The effect of wet casting thickness was determined using 9% HPC films loaded with 6% LHC. Metrics for this study are shown in Table 2. Films were incubated in 4 mL of SVF+2% solutol at room temperature. Results showed that the 2 mm and 3 mm wet casted films exhibited similar release profiles with 100% LHC release in 30-40 minutes, while the thicker films casted at 4 mm and 5 mm exhibited slower release kinetics reaching complete LHC release in 90 minutes (FIG. 7B).

Figure 7C:
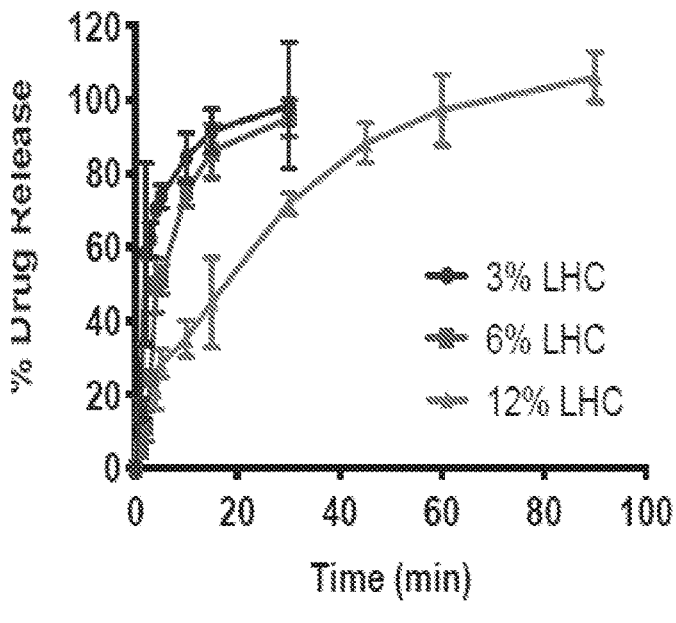

The effect of drug loading was determined using 9% HPC casted at a constant wet thickness (5 mm) and varying drug loading amounts (3%, 6%, 12% LHC in solution formulation) (Table 5). Results show that the 3% and 6% LHC loaded films had similar drug release kinetics, both reaching 100% drug release in about 30 minutes. The 12% LHC loaded films had an extended drug release, reaching 100% in 90 minutes (FIG. 7C).

Figure 7D:
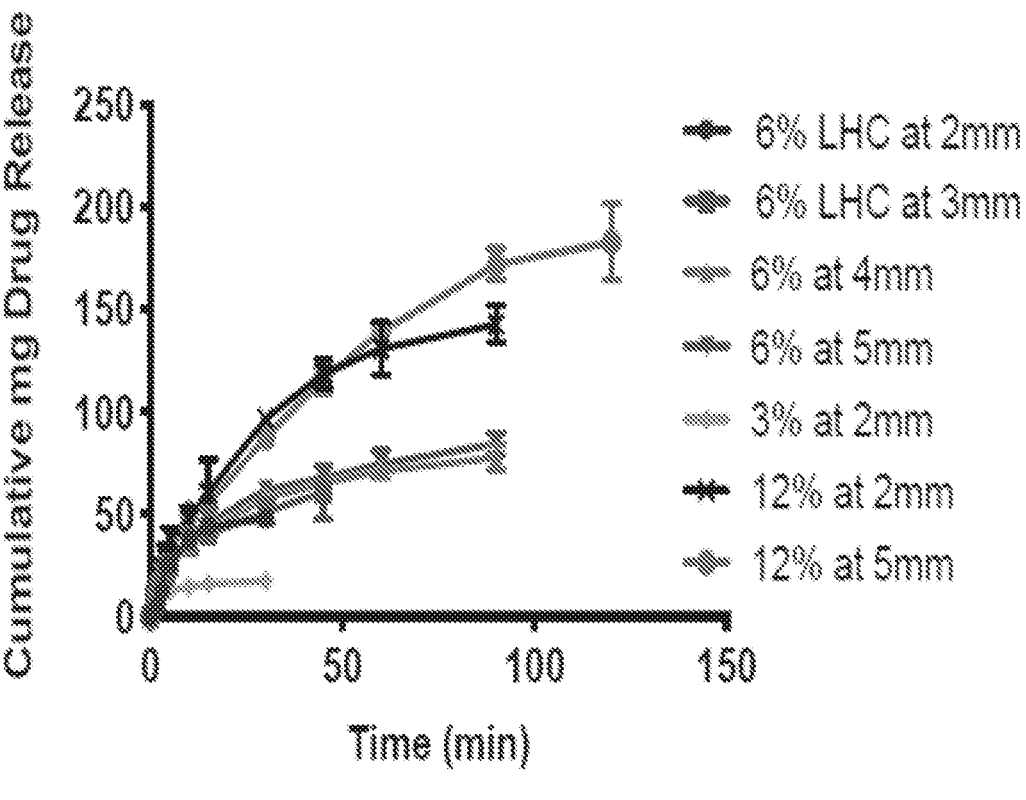

The 9% HPC films were optimized to extend LHC release duration to 120 minutes. This was done by increasing the drug loading amount to 12% and the wet casting thickness to 5 mm. This combination of parameters provided a synergistic effect to obtain a steady release of LHC over 120 min (FIG. 7D). Finally, the drug release and dissolution rates were compared using 9% HPC 6% LHC films. Results demonstrated that LHC release was independent of the film dissolution rate, and LHC mainly released via diffusion out of the film (FIGS. 14A-14L).

TABLE 5

Effect of wet casted thickness and drug loading on drug release kinetics. To compare the effect
of wet casted thickness the amount of drug was held constant in each film. To compare the effect
of drug loading the wet casting thickness was held constant for each film formulation.

| | Solution Formulation | wt % drug loading in Solution Formulation | Wet Casted Thickness (mm) | Dry Film Thickness (μm) | Weight of Drug Loaded Dry Film (mg) |
|---|---|---|---|---|---|
| Effect of Wet Casted Thickness | 9% HPC | 6% | 2 | 249.23 ± 0.03 | 118.32 ± 4.26 |
| | | 6% | 3 | 303.57 ± 0.02 | 128.5 ± 10.28 |
| | | 6% | 4 | 349.06 ± 0.04 | 179.0 ± 6.68 |
| | | 6% | 5 | 511.17 ± 0.03 | 198.4 ± 10.25 |
| Effect of Drug Loading | 9% HPC | 3% | 5 | 423 ± 0.02 | 69.88 ± 5.75 |
| | | 6% | 5 | 520 ± 0.03 | 118.32 ± 4.26 |
| | | 12% | 5 | 728 ± 0.05 | 225.08 ± 10.87 |

Example 9

In Vivo Mouse Safety Studies

All in vivo studies were performed in BALB/c mice. Eight-week (20-25 g) female BALB/c mice were purchased from The Jackson Laboratory (Bar Harbor, ME). The procedures were performed in accordance with the guidelines for animal experimentation by the Institutional Animal Care and Use Committee, School of Medicine, University of North Carolina at Chapel Hill.

Figure 8:
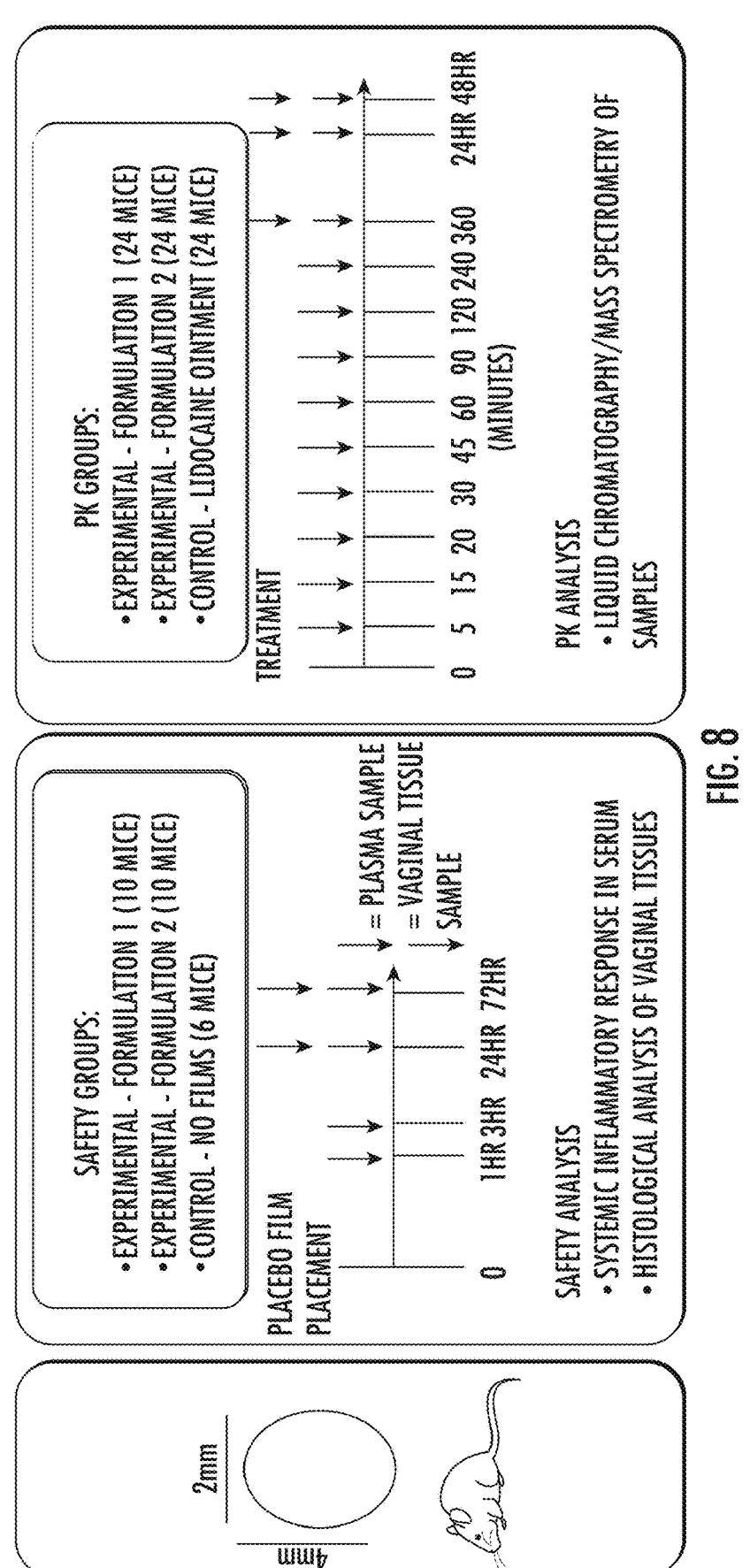
FIG. 8 is a schematic illustration of in vivo mouse safety studies to assess systemic and local toxicity of placebo films made with 5% HEC and 9% HPC formulations.
Figures 9A, 9B:
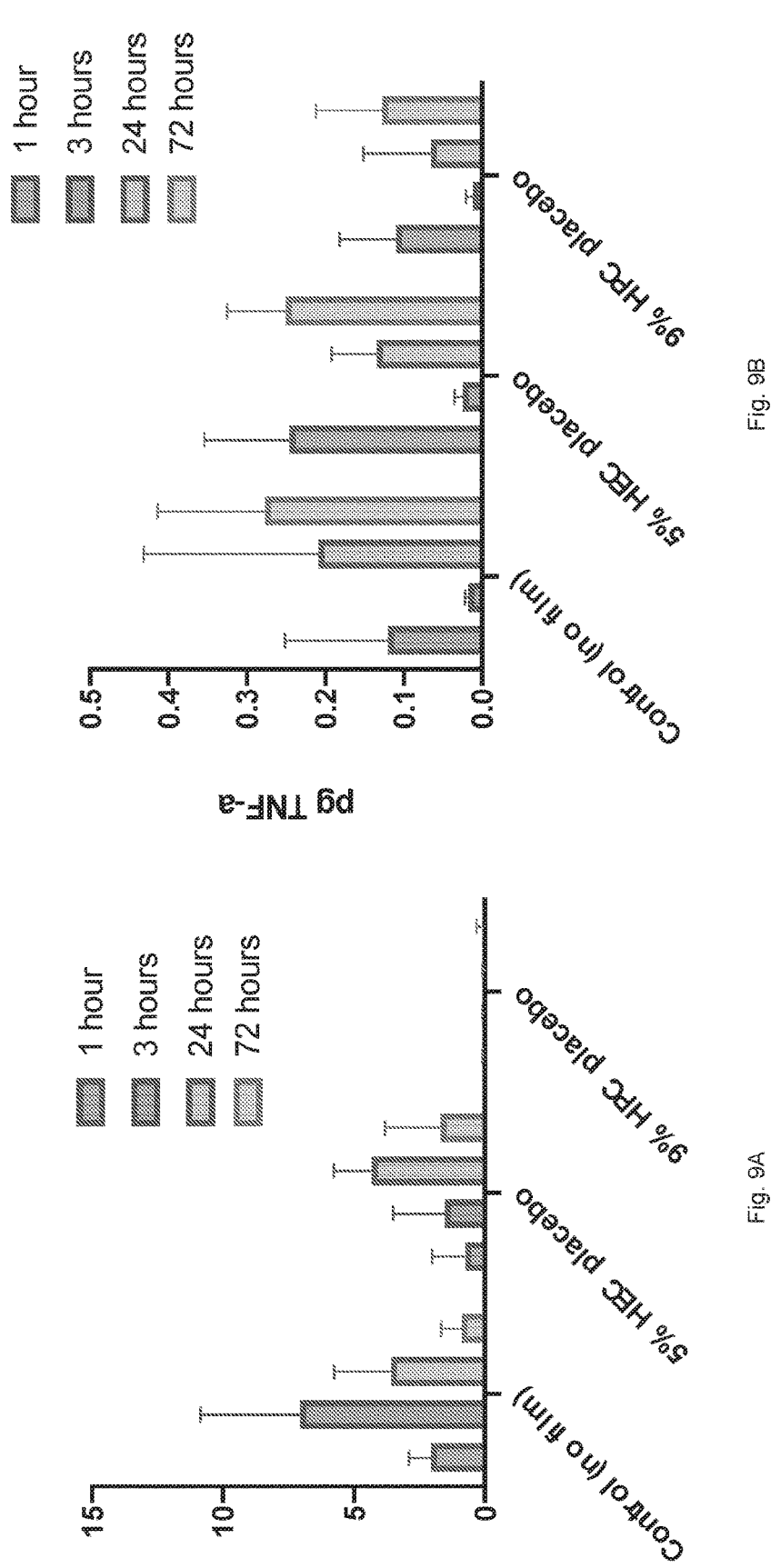
FIGS. 9A-9B show in vivo safety evaluation of 5% HEC and 9% HPC in BALB/c mice (n=10 per group). Concentration of IL-6 (pg/mL) and TNF-α (pg/mL) in plasma post-film implantation quantified by ELISA (n=5 per group).

A 72 h in vivo study was carried out to assess the safety and in vivo biodegradation of two placebo film formulations (5% HEC and 9% HPC) in female BALB/c mice (6-8 weeks, Jackson Laboratory) (FIG. 8). Local inflammation of vaginal tissues was evaluated using H&E histological analysis. Placebo films (4 mm diameter) were administered intravaginally in mice and mice were monitored for signs of inflammation (body weight, grooming, other signs). At 1, 3, 24, and 72 h post film administration, blood samples (n=5 per time point) were collected into capillary tubes and stored at –80° C. to quantify pro-inflammatory cytokines including tumor necrosis factor alpha (TNF-α) and interleukin-6 (IL-6) by enzyme-linked immunosorbent assay (ELISA, MAX™ Deluxe sets, BioLegend®). At 24 h and 72 h mice were sacrificed (n=5 at each time point), blood samples via heart puncture and implant site tissues were collected into capillary tubes and stored at –80° C. to quantify pro-inflammatory cytokines (FIGS. 9A-9B). Mice were subsequently necropsied by intracardiac injection of 4% paraformaldehyde (pH 7.3) and the vaginal tissues were harvested for histology by submerging tissue in 10% neutral buffered formalin at a ratio of 1:10 tissue-fixative at room temperature for 72 h, and then transferred to room temperature 70% ethyl alcohol. Tissues were processed, paraffin embedded, sectioned at 5-μm thick, and stained by routine hematoxylin and eosin (H&E) for histopathological examination (LCCC Animal Histopathology Core Facility at the University of North Carolina at Chapel Hill).

Example 10

Results and Discussion

Thin films for the release of lidocaine HCl (LHC) for temporary pain relief of VBD were developed, characterized, and evaluated in vitro for their potential use as a new treatment option. The research methods selected for evaluation of these films were chosen based on the end goal key criteria for the films as a drug delivery product that will have high user acceptability and preferred characteristics, while providing the necessary therapeutic effect. When compared to the lidocaine ointment currently used as a first line treatment for VBD, the main goals for this thin film product are improved ease of application, comfort, prolonged pain relief, enhanced efficacy in pain relief via increased precision and retention of drug at target site.

These results herein confirm the development of a mucoadhesive biodissolvable thin film that achieves the aforementioned goals and provides a new treatment option for VBD. The mucoadhesive properties of the final film can be influenced by a number of different properties of the formulation including polymer properties (hydrophilicity, molecular weight, cross-linking), pH, concentration of polymer, and drug loading. Differences in mucoadhesive properties of films prepared with different polymer types was attributed to potential differences in the cross-link density of the polymer network given the similarities in their physical and chemical properties, pH, and molecular weights. The increase in elasticity (% strain) with the presence of lidocaine for the 9% HPC films was attributed to presence of hydrogen bonding interactions between drug and polymer resulting in a stronger and more elastic film compared to the drug-free film.

Film properties including mechanical properties, mucoadhesive properties and dissolution rate are contributing factors to the comfort and prolonged pain relief of the film. Given that the properties of the vulva (pH, presence of mucin, etc.) can vary amongst women as well as for an individual woman, it is necessary to consider that the VBD treatment film is robust enough to have the same therapeutic effect across these differences. Film dissolution rate was found to be pH independent, and while the presence of mucin in the dissolution media increased the rate of dissolution the resulting dissolution rate was still in line with the translational target. True comparison of the effect of polymer type on dissolution rate was not possible due to the inability to control for the dried film thickness despite the ability to control for the wet casting thickness during film fabrication. However, investigating various polymer types provided information on dissolution rates for each polymer and how the rates can differ based on polymer type. Based on these results, the HPC films dissolved the fasted, whereas HPMC films took the longest to fully dissolve, and HEC films had intermediate dissolution rates. Dissolving cellulose-based materials is reliant on breaking the hydrogen bonded network of cellulose chains (Zhang et al., 2014), so the faster dissolution of HPC indicates weaker hydrogen bonding. These results are similar to dissolution efficiency results studied by Chowdary et. al. (Chowdary & Suresh Babu, 1994). Understanding the parameters that contribute to differences in dissolution rates allows the ability to tune and optimize film properties to achieve target outcomes.

Ideally these films designed as a treatment of VBD need to be flexible to provide a comfortable feel for women when applied to the vulva, but also strong enough to allow proper handling and to use. Results from the mechanical testing of various films showed a significant difference in strain at time of fracture for films containing lidocaine compared to their placebo analogues indicating that the drug loaded films were much more likely to stretch under tensile forces, while the placebo films were more brittle and more likely to break when stretched. For anatomical use having a film that can stretch to meet anatomical constraints, adapt based on external pressures to the vulva, or during time of application is critical for an effective treatment option for VBD.

Increased precision of delivering lidocaine to the target site and retention of the drug in the target tissue is dependent on the drug release kinetics as well as drug diffusion through the target tissue. Two film formulations were investigated and developed. One film was designed for short-term use prior to intercourse to allow complete LHC release within 5 min. Another film was designed to provided sustained release of LHC over 120 min for prolonged pain relief. To achieve the instant release of drug, HEC films are ideal for a 'stick and remove' approach where the film is placed on the vulva for 5 min to deliver entire amount of LHC and removed after 5 min. The 5% HEC film is ideal for the short-term application based on its slow in vitro dissolution rate (~5% within 5 min) and fast release of LHC from the film upon contact with the release media (100% release in 5 min). To achieve a more sustained release of LHC, HPC films were optimized and provided sustained release of LHC over 120 min at a target therapeutic dose (~50 mg LHC) extrapolated from the dose administered using the lidocaine ointment currently used as a standard of care for VBD. Future studies will evaluate these two films in vivo in a mouse model to assess the in vivo safety and pharmacokinetics of the 5% HEC film for short-term LHC release (5 min), and the 9% HPC film for prolonged LHC release (120 min).

Safety and biocompatibility of implantable drug delivery devices are essential in development of a drug delivery system. Results from a 72 h in vivo safety study showed that the two film formulations tested (5% HEC, 9% HPC) were well tolerated and mice did not show any signs of overt toxicity, behavioral changes, water consumption or weight loss. Results from the ELISA assay, quantifying levels of TNF-$\alpha$ and IL-6 pro-inflammatory cytokines in plasma from peripheral blood collections, showed that no systemic acute, or chronic inflammation was present in both treatment groups. IL-6 proinflammatory cytokines in plasma were in the range of 0-4 pg/mL and were comparable or lower than IL-6 levels in plasma of sham mice (FIG. 9A). Similarly, TNF-$\alpha$ proinflammatory cytokines levels in plasma were the range of 0-0.25 pg/mL in all film groups and were comparable to sham mice (FIG. 9B). These results demonstrate that the film formulations are well-tolerated in vivo with no significant inflammation, weight loss or other signs of toxicity.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

Abo Enin HA, E. N. N., Elmonem RA. (2017). Treatment of Radiation-Induced Oral Mucositis Using a Novel Accepted Taste of Prolonged Release Mucoadhesive Bi-medicated Double-Layer Buccal Films. *AAPS PharmSciTech,* 18(2), 563-575.

Aerts, L., Bergeron, S., Corsini-Munt, S., Steben, M., & Paquet, M. (2015). Are Primary and Secondary Provoked Vestibulodynia Two Different Entities? A Comparison of Pain, Psychosocial, and Sexual Characteristics. *The Journal of Sexual Medicine,* 12(6), 1463-1473. doi:10.1111/jsm.12907

Akil, A., Agashe, H., Dezzutti, C. S., Moncla, B. J., Hillier, S. L., Devlin, B., . . . Rohan, L. C. (2015). Formulation and Characterization of Polymeric Films Containing Combinations of Antiretrovirals (ARVs) for HIV Prevention. *Pharmaceutical Research,* 32(2), 458-468. doi:10.1007/s11095-014-1474-4

Brian Button, H. P. G., Eyad Atieha, Yu-Cheng Chena, Robert Williamsa, Siddharth Shenoy, Elijah Lackeya, Nathan T. Shenkutea, Li-Heng Caid, e, Robert G. Dennisc, Richard C. Bouchera, and Michael Rubinstein. (2018). Roles of mucus adhesion and cohesion incough clearance. *PNAS,* 115(49), 12501-12506. doi:10.1073/pnas.1811787115

Bunge, K. E., Dezzutti, C. S., Rohan, L. C., Hendrix, C. W., Marzinke, M. A., Richardson-Harman, N., . . . Hillier, S. L. (2016). A Phase 1 Trial to Assess the Safety, Acceptability, Pharmacokinetics, and Pharmacodynamics of a Novel Dapivirine Vaginal Film. *JAIDS Journal of Acquired Immune Deficiency Syndromes,* 71(5), 498-505. doi:10.1097/qai.0000000000000897

Chowdary, K. P. R., & Suresh Babu, K. V. V. (1994). Dissolution, Bioavailability and Ulcerogenic Studies on Solid Dispersions of Indomethacin in Water Soluble Cellulose Polymers. *Drug Development and Industrial Pharmacy,* 20(5), 799-813. doi:10.3109/03639049409038332

Ciszek, B. P., Khan, A. A., Dang, H., Slade, G. D., Smith, S., Bair, E., . . . Nackley, A. G. (2015). MicroRNA expression profiles differentiate chronic pain condition subtypes. 166(6), 706-720.e711. doi:10.1016/j.trsl.2015.06.008

Cook, M. T., & Brown, M. B. (2018). Polymeric gels for intravaginal drug delivery. *Journal of Controlled Release,* 270, 145-157. doi:10.1016/j.jconrel.2017.12.004

De Araujo Pereira, R. R., & Bruschi, M. L. (2012). Vaginal mucoadhesive drug delivery systems. 38(6), 643-652. doi:10.3109/03639045.2011.623355

Fan, M. D., Kramzer, L. F., Hillier, S. L., Chang, J. C., Meyn, L. A., & Rohan, L. C. (2016). Preferred Physical Characteristics of Vaginal Film Microbicides for HIV Prevention in Pittsburgh Women. doi:10.1007/s10508-016-0816-1

Gipson, I. K., Moccia, R., Spurr-Michaud, S., Argueso, P., Gargiulo, A. R., Hill, J. A., . . . Keutmann, H. T. (2001). The Amount of MUC5B Mucin in Cervical Mucus Peaks at Midcycle 1. 86(2), 594-600. doi:10.1210/jcem.86.2.7174

Goodell, H. P., Shenoy, S. K., Shenkute, N. T., Lackey, E., Dennis, R. G., & Button, B. (2019). Adhesive and Cohesive Peel Force Measurement of Human Airway Mucus. Bio-protocol, 9(13).

Haefner, H. K., Collins, M. E., Davis, G. D., Edwards, L., Foster, D. C., Hartmann, E. H., . . . Wilkinson, E. J.

(2005). The Vulvodynia Guideline. *Journal of lower genital tract disease,* 9(1), 40-51. doi:10.1097/00128360-200501000-00009

Harlow BL, E. S. (2003). A population-based assessment of chronic unexplained vulvar pain: have we underestimated the prevalence of vulvodynia? *J Am Med Womens Assoc,* 58(2), 82-88.

Johal, H. S., Garg, T., Rath, G., & Goyal, A. K. (2016). Advanced topical drug delivery system for the management of vaginal candidiasis. 23(2), 550-563. doi:10.3109/10717544.2014.928760

Karki, S., Kim, H., Na, S.-J., Shin, D., Jo, K., & Lee, J. (2016). Thin films as an emerging platform for drug delivery. *Asian Journal of Pharmaceutical Sciences,* 11(5), 559-574. doi:10.1016/j.ajps.2016.05.004

Landry, T., Bergeron, S., Dupuis, M.-J., & Desrochers, G. (2008). The Treatment of Provoked Vestibulodynia. *The Clinical Journal of Pain,* 24(2), 155-171. doi:10.1097/ajp.0b013e31815aac4d Machado, R. M., Palmeira-De-Oliveira, A., Martinez-De-Oliveira, J., & Palmeira-De-Oliveira, R. (2013). Vaginal Films for Drug Delivery. 102(7), 2069-2081. doi:10.1002/jps.23577

Notario-Pérez, F., Martin-Illana, A., Cazorla-Luna, R., Ruiz-Caro, R., Bedoya, L.-M., Peña, J., & Veiga, M.-D. (2019). Development of mucoadhesive vaginal films based on HPMC and zein as novel formulations to prevent sexual transmission of HIV. *International Journal of Pharmaceutics,* 570, 118643. doi:10.1016/j.ijpharm.2019.118643

Padula, C., Pozzetti, L., Traversone, V., Nicoli, S., & Santi, P. (2013). In Vitro Evaluation of Mucoadhesive Films for Gingival Administration of Lidocaine. *AAPS PharmSciTech,* 14(4), 1279-1283. doi:10.1208/si2249-013-0020-8

Preis, M., Woertz, C., Schneider, K., Kukawka, J., Broscheit, J., Roewer, N., & Breitkreutz, J. (2014). Design and evaluation of bilayered buccal film preparations for local administration of lidocaine hydrochloride. *European Journal of Pharmaceutics and Biopharmaceutics,* 86(3), 552-561. doi:10.1016/j.ejpb.2013.12.019

Pukall, C. F. (2016). Primary and Secondary Provoked Vestibulodynia: A Review of Overlapping and Distinct Factors. *Sexual Medicine Reviews,* 4(1), 36-44. doi:10.1016/j.sxmr.2015.10.012

Roh, J., Han, M., Kim, K.-N., & Kim, K.-M. (2016). The *in vitro* and *in vivo* effects of a fast-dissolving mucoadhesive bi-layered strip as topical anesthetics. *Dental Materials Journal,* 35(4), 601-605. doi:10.4012/dmj.2015-369

Samuel, H., Yalkowsky, H., & Jain, P. (2003). Handbook of aqueous solubility data. In: CRC Press: Boca Raton, FL.

Shaikh, R., Raj Singh, T. R., Garland, M. J., Woolfson, A. D., & Donnelly, R. F. (2011). Mucoadhesive drug delivery systems. In *J Pharm Bioallied Sci* (Vol. 3, pp. 89-100).

Sobel, J. (2016). Patient education: Vaginal discharge in adult women (Beyond the Basics). Uptodate.com.

Susan Kellogg Spadt, C., PhDSheryl Kingsberg, PhD. (April 2020). Treatment of vulvodynia (vulvar pain of unknown cause). In: UpToDate.

Valenta, C. (2005). The use of mucoadhesive polymers in vaginal delivery. *Advanced Drug Delivery Reviews,* 57(11), 1692-1712. doi:10.1016/j.addr.2005.07.004

Xie, Y., Shi, L., Xiong, X., Wu, E., Veasley, C., & Dade, C. (2012). Economic burden and quality of life of vulvodynia in the United States. *Current Medical Research and Opinion,* 28(4), 601-608. doi:10.1185/03007995.2012.666963

Zhang, C., Liu, R., Xiang, J., Kang, H., Liu, Z., & Huang, Y. (2014). Dissolution mechanism of cellulose in N, N-dimethylacetamide/lithium chloride: revisiting through molecular interactions. *The Journal of Physical Chemistry B,* 118(31), 9507-9514.

Zolnoun, D., Park, E. M., Moore, C. G., Liebert, C. A., Tu, F. F., & As-Sanie, S. (2008). Somatization and psychological distress among women with vulvar vestibulitis syndrome. *International Journal of Gynecology & Obstetrics,* 103(1), 38-43. doi:10.1016/j.ijgo.2008.05.016

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A biodissolvable film for localized treatment of a disorder of the female genital tract, the biodissolvable film comprising an active ingredient integrated and/or loaded into the biodissolvable film, wherein the active ingredient comprises lidocaine hydrochloride (LHC);

wherein the biodissolvable film is prepared by (i) casting a formulation comprising the active ingredient and about 3% w/w high molecular weight (HMW) hydroxyethyl cellulose (HEC) to about 5% w/w HMW HEC to provide a wet cast film, wherein the HMW HEC is HEC with a molecular weight of about 250 kilodaltons, and (ii) drying the wet cast film to provide the biodissolvable film; and wherein the biodissolvable film comprises a mucoadhesive property and forms a substantially u-shaped profile or substantially v-shaped profile, the substantially u-shaped or substantially v-shaped biodissolvable film configured for application to a vulvar vestibule of the female genital tract.

2. The biodissolvable film of claim 1, wherein the profile of the biodissolvable film is of a size ranging from about 3 cm to about 5 cm long, and about 2 cm to about 4 cm wide, wherein the biodissolvable film has a wet thickness of about 2, 3, 4 or 5 mm.

3. The biodissolvable film of claim 1, wherein the biodissolvable film is substantially biocompatible as defined by causing less than about 5% cell death and/or cell damage when exposed to a cell or tissue.

4. The biodissolvable film of claim 1, wherein the active ingredient is loaded at a rate of about 3% to about 12%.

5. The biodissolvable film of claim 1, wherein the biodissolvable film is configured to treat inflammatory disorders, atrophic disorders, pain disorders and/or irritative disorders of the female genital tract.

6. The biodissolvable film of claim 1, wherein the biodissolvable film is configured to treat Vestibulodynia (VBD).

7. The biodissolvable film of claim 1, wherein the LHC is loaded into the film at a rate of about 6% and wherein the film has a wet thickness of about 2 mm.

8. The biodissolvable film of claim 1, wherein the biodissolvable film is prepared by (i) casting a formulation comprising the active ingredient and about 5% w/w HMW HEC to provide a wet cast film having a thickness of about 2 mm, and (ii) drying the wet cast film to provide the biodissolvable film.

9. The biodissolvable film of claim 1, wherein the biodissolvable film exhibits 100% release of the active ingredient in 5 minutes in simulated vaginal fluid (SVF).

10. A method of treating an inflammatory, atrophic, painful, and/or irritative disorders of the female genital tract, the method comprising:

providing a subject in need of treatment; and applying a biodissolvable film of claim 1 to the subject, wherein the biodissolvable film is applied to the vulvar vestibule of the subject.

11. The method of claim 10, wherein the inflammatory, atrophic, painful and/or irritative disorder comprises Vestibulodynia (VBD).

12. A biodissolvable film for localized treatment of a disorder of the female genital tract, the biodissolvable film comprising an active ingredient integrated and/or loaded into the biodissolvable film, wherein the active ingredient comprises lidocaine hydrochloride (LHC) loaded into the biodissolvable film at a rate of about 12%;

wherein the biodissolvable film is prepared by (i) casting a formulation comprising the active ingredient and about 7% w/w hydroxypropyl cellulose (HPC) to about 9% w/w HPC to provide a wet cast film having a wet thickness of about 4 mm or 5 mm and (ii) drying the wet cast film to provide the biodissolvable film; and wherein the biodissolvable film comprises a mucoadhesive property and forms a substantially u-shaped profile or substantially v-shaped profile, the substantially u-shaped or substantially v-shaped biodissolvable film configured for application to a vulvar vestibule of the female genital tract.

13. The biodissolvable film of claim 12, wherein the profile of the biodissolvable film is of a size ranging from about 3 cm to about 5 cm long, and about 2 cm to about 4 cm wide.

14. The biodissolvable film of claim 12, wherein the biodissolvable film is substantially biocompatible as defined by causing less than about 5% cell death and/or cell damage when exposed to a cell or tissue.

15. The biodissolvable film of claim 12, wherein the biodissolvable film is prepared by (i) casting a formulation comprising about 9% w/w HPC and about 12% w/w LHC to provide a wet cast film having a thickness of about 5 mm and (ii) drying the wet cast film to provide the biodissolvable film.

16. The biodissolvable film of claim 12, wherein the biodissolvable film exhibits an extended release duration of the active ingredient in simulated vaginal fluid (SVF), wherein the extended release duration is about 120 minutes.

17. A method of treating an inflammatory, atrophic, painful, and/or irritative disorders of the female genital tract, the method comprising:

providing a subject in need of treatment; and applying a biodissolvable film of claim 12 to the subject, wherein the biodissolvable film is applied to the vulvar vestibule of the subject.

18. The method of claim 17, wherein the inflammatory, atrophic, painful and/or irritative disorder comprises Vestibulodynia (VBD).

* * * * *